United States Patent
Braun et al.

(10) Patent No.: US 6,500,213 B1
(45) Date of Patent: Dec. 31, 2002

(54) OXIDIZING HAIR COLORING AGENTS CONTAINING 2,5-DIAMINO-1-PHENYLBENZENE DERIVATIVES AND NOVEL 2,5-DIAMINO-1-PHENYLBENZENE DERIVATIVES

(75) Inventors: Hans-Juergen Braun, Ueberstorf (CH); Laurent Chassot, Praroman (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/446,726

(22) PCT Filed: Feb. 19, 1999

(86) PCT No.: PCT/EP99/01084

§ 371 (c)(1),
(2), (4) Date: Mar. 14, 2000

(87) PCT Pub. No.: WO99/59527

PCT Pub. Date: Nov. 25, 1999

(30) Foreign Application Priority Data

May 16, 1998 (DE) .......................... 198 22 041

(51) Int. Cl.$^7$ ................................. A61K 7/13
(52) U.S. Cl. ............. 8/405; 8/405; 8/406; 8/407; 8/409; 8/410; 8/411
(58) Field of Search ............... 8/408, 409, 410, 8/411, 405, 407

(56) References Cited

FOREIGN PATENT DOCUMENTS

DE 2518393 * 4/1976
JP 59220733 * 12/1984

* cited by examiner

*Primary Examiner*—Yogendra N. Gupta
*Assistant Examiner*—Eisa Elhilo
(74) *Attorney, Agent, or Firm*—Michael J. Striker

(57) ABSTRACT

The object of the present patent application are agents for the oxidative coloring of keratin fibers, particularly hair, based on a developer-coupler combination, characterized in that they contain as the developer at least one 2,5-diamino-1-phenylbenzene derivative of general formula

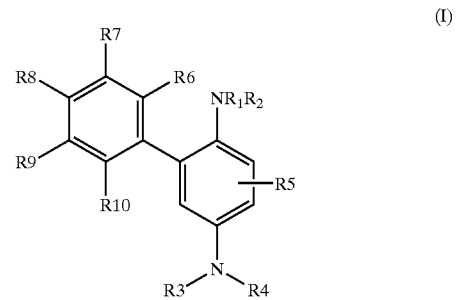

and novel 2,5-diamino-1-phenylbenzene derivatives of formula (I) wherein at least one of the R1 to R10 radicals is different from hydrogen.

14 Claims, No Drawings

OXIDIZING HAIR COLORING AGENTS CONTAINING 2,5-DIAMINO-1-PHENYLBENZENE DERIVATIVES AND NOVEL 2,5-DIAMINO-1-PHENYLBENZENE DERIVATIVES

The present invention relates to agents for oxidative coloring of keratin fibers, particularly human hair, based on a developer/coupler combination and which contain as the developer a 2,5-diamino-1-phenylbenzene derivative and to novel 2,5-diamino-1-phenylbenzene derivatives.

Oxidation dyes have become very important for the coloring of keratin fibers, particularly in the field of hair coloring. In this case, the color is created by reaction of certain developers with certain couplers in the presence of an appropriate oxidant. Suitable developers for this purpose are, in particular, 2,5-diaminotoluene, 2,5-diaminophenylethyl alcohol, p-aminophenol and 1,4-diaminobenzene. Suitable couplers are, for example, resorcinol 4-chlororesorcinol, 1-naphthol, 3 aminophenol and derivatives of m-phenylenediamine.

Oxidation dyes used for coloring human hair must meet many special requirements besides producing colorations of a desired intensity. The dyes must be toxicologically and dermatologically harmless, and the resulting hair colors must have good light, permanent wave, acid and rubbing resistance. The hair colors must also remain stable for a period of at least four to six weeks in the absence of light, rubbing and chemicals. In addition, it must be possible, by means of a combination of appropriate developers and couplers, to create a wide range of different color shades.

Currently used coloring agents, however, do not meet the aforesaid requirements in all respects.

Hence, a need continues to exist for novel developers which will meet the aforesaid requirements to a high degree.

In this regard, we have now found that 1,4-diaminobenzene derivatives of general formula (I) meet the requirements placed on developer components to an unusually high degree. Thus, by use of such developer components together with known coupler components, intense color shades are obtained which are unusually resistant to light and washing.

The object of the present invention are agents for oxidative coloring of keratin fibers, for example wool, furs, feathers or hair, particularly human hair, based on a developer-coupler combination containing as the developer a 2,5-diamino-1-phenylbenzene derivative of general formula (I)

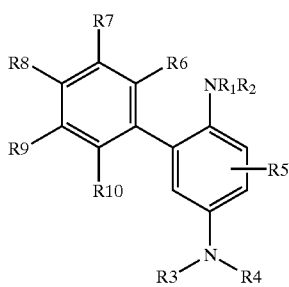

(I)

wherein
R1, R2, R3 and R4 independently of each other denote hydrogen, a $C_1$–$C_6$ alkyl, $C_1$–$C_4$ hydroxyalkyl, $C_2$–$C_4$ dihydroxyalkyl or $C_1$–$C_4$ alkoxy-($C_1$–$C_4$)alkyl group, or R1 and R2 or R3 and R4 form a four-membered to eight-membered aliphatic ring, with at least two of the R1 to R4 groups denoting hydrogen;

R5 denotes hydrogen, a hydroxyl group, a halogen atom or a $C_1$–$C_4$ alkyl, $C_1$–$C_4$ hydroxyalkyl or $C_1$–$C_4$ alkoxy group;

R6, R7, R8, R9 and R10 independently of each other denote hydrogen, a halogen atom or a cyano, hydroxyl, $C_1$–$C_4$ alkoxy, $C_1$–$C_8$ alkyl, $C_1$–$C_4$ alkyl thioether, mercapto, nitro, amino, alkylamino, dialkylamino, trifluoromethane, —C(OH), —C(O)CH$_3$, —C(O)CF$_3$, —Si(CH$_3$)$_3$, $C_1$–$C_4$ hydroxyalkyl, $C_1$–$C_4$ dihydroxyalkyl, —CH=CHR11 or —(CH$_2$)$_p$—CO$_2$R12 group or a —(CH$_2$)$_p$—R13 group, where p=1, 2, 3 or 4, or a —C(R14)=NR15 group or a C(R17)H—NR18R19 group, or two adjacent R6 to R10 groups form a —O—CH$_2$—O bridge;

R11 denotes hydrogen, a hydroxyl, nitro, amino, CO$_2$R12 or —C(O)CH$_3$ group;

R12, R14 and R17 independently od each other denote hydrogen or a $C_1$–$C_4$ alkyl group;

R13 denotes an amino or nitrile group;

R15, R18 and R19 independently of each other denote hydrogen, a hydroxyl, $C_1$–$C_4$ alkyl, $C_1$–$C_4$ hydroxyalkyl or $C_3$–$C_4$ dihydroxyalkyl group or a radical of formula

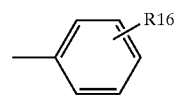

R16 denotes hydrogen, an amino group or a hydroxyl group, or containing a the physiologically tolerated, water-soluble salt thereof.

Suitable compounds of formula (I) are, for example:
2,5-diamino-1-phenylbenzene; 2,5-diamino-1-(4-bromophenyl)benzene; 2,5-diamino-1-phenyl-1-(4-ethenylphenyl)benzene; 2,5-diamino-1-(2,3,4-trimethoxyphenyl)benzene; 2,5-diamino-1-[2,4-di(2-hydroxyethyl)aminophenyl]benzene; 2,5-diamino-1-(2,4-diaminophenyl)benzene; 2,5-diamino-1-(2,4-dihydroxyphenyl)benzene; 2,5-diamino-1-(2,4-dimethylaminophenyl)benzene; 2,5-diamino-1-(2,4-methoxyphenyl)benzene; 2,5-diamino-1-[2,5-di(2-hydroxyethyl)aminophenyl]benzene; 2,5-diamino-1-(2,5-diaminophenyl)benzene; 2,5-diamino-1-(2,5-dihydroxyphenyl)benzene; 2,5-diamino-1-(2,5-dimethoxyphenyl)benzene; 2,5-diamino-1-(2,5-dimethylaminophenyl)benzene; 2,5-diamino-1-[2,6-di(2-hydroxyethyl)aminophenyl; 2,5-diamino-1-(2,6-diaminophenyl]benzene; 2,5-diamino-1-(2,6-dihydroxyphenyl)benzene; 2,5-diamino-1-(2,6-dimethoxyphenyl)benzene; 2,5-diamino-1-(2,6-dimethylaminophenyl)benzene; 2,5-diamino-1-[2-(bromomethyl)phenyl]benzene; 2,5-diamino-1-(2-amino-5-hydroxyphenyl)-benzene; 2,5-diamino-1-(2-aminophenyl)benzene; 2,5-diamino-1-(2-carboxyphenyl)benzene; 2,5-diamino-1-(2-chlorophenyl)benzene; 2,5-diamino-1-[2-di(2-hydroxyethyl)aminophenyl]benzene; 2,5-diamino-1-(2-dimethylaminophenyl)benzene; 2,5-diamino-1-(2-fluorophenyl)benzene; 2,5-diamino-1-(2-formylphenyl)benzene; 2,5-diamino-1-(2-hydroxy-4-aminophenyl)benzene; 2,5-diamino-1-(2-hydroxy-5-aminophenyl)benzene; 2,5-diamino-1-(2-hydroxyphenyl)benzene; 2,5-diamino-1-(2-methoxyphenyl)benzene; 2,5-diamino-1-(2-methylphenyl)benzene; 2,5-diamino-1-(2-nitrophenyl)benzene; 2,5-diamino-1-(2-trifluoromethylphenyl)benzene;

2,5-diamino-1-[3,5-di(2-hydroxyethyl)aminophenyl]benzene; 2,5-di-amino-1-(3,5-diaminophenyl)benzene; 2,5-diamino-1-(3,5-dihydroxyphenyl)benzene; 2,5-diamino-1-(3,5-dihydroxyphenyl)benzene; 2,5-diamino-1-(3,5-dimethylaminophenyl)benzene; 2,5-diamino-1-(3-aminophenyl)benzene; 2,5-diamino-1-(3-bromophenyl)benzene; 2,5-diamino-1-(3-carboxyphenyl)benzene; 2,5-diamino-1-(3-chlorophenyl)benzene; 2,5-diamino-1-[3-di(2-hydroxyethyl)aminophenyl]benzene; 2,5-diamino-1-(3-dimethylaminophenyl)benzene; 2,5-diamino-1-(3-fluorophenyl)benzene; 2,5-diamino-1-(3-formylphenyl)benzene; 2,5-diamino-1-(3-hydroxy-5-aminophenyl)benzene; 2,5-diamino-1-(3-hydroxy-phenyl)benzene; 2,5-diamino-1-(3-methoxyphenyl)benzene; 2,5-diamino-1-(3-nitrophenyl)benzene; 2,5-diamino-1-(3-fluoromethylphenyl)benzene; 2,5-diamino-1-[4-(dimethylamino)phenyl]benzene; 2,5-diamino-1-[4-(hydroxymethyl)phenyl]benzene; 2,5-diamino-1-[4-(methylthio)phenyl]benzene; 2,5-diamino-1-[4-(trifluoromethyl)phenyl]benzene; 2,5-diamino-1-[4-(trimethylsilyl)phenyl]benzene; 2,5-diamino-1-(4-acetylphenyl)benzene; 2,5-diamino-1-(4-aminophenyl)benzene; 2,5-diamino-1-(4-carboxyphenyl)benzene; 2,5-diamino-1-(4-chlorophenyl)benzene; 2,5-diamino-1-[4-(di(2-hydroxyethyl)aminophenyl]benzene; 2,5-diamino-1-(4-dimethylaminophenyl)benzene; 2,5-diamino-1-(4-ethoxyphenyl)benzene; 2,5-diamino-1-(4-fluorophenyl)benzene; 2,5-diamino-1-(4-formylphenyl)benzene; 2,5-diamino-1-(4-hydroxyphenyl)benzene; 2,5-diamino-1-(4-methoxyphenyl)benzene; 2,5-diamino-1-(4-methylphenyl)benzene; 2,5-diamino-1-phenylbenzene; 2,5-diamino-4-chloro-1-phenylbenzene; 2,5-diamino-4-methoxy-1-phenylbenzene; 2,5-diamino-4-methyl-1-phenylbenzene; 2-amino-5-(2,3-dihydroxypropyl)amino-1-(2,3,4-trimethoxyphenyl)benzene; 2-amino-5-(2,3-dihydroxypropyl)amino-1-(2,4-dihydroxyphenyl)-benzene; 2-amino-5-(2,3-dihydroxypropyl)amino-1-(2,5-diaminophenyl)benzene; 2-amino-5-(2,3-dihydroxypropyl)amino-1-(2,6-dimethoxyphenyl)benzene; 2-amino-5-(2,3-dihydroxypropyl)amino-1-(2-amino-5-hydroxyphenyl)benzene; 2-amino-5-(2,3-dihydroxypropyl)amino-1-(2-aminophenyl)benzene; 2-amino-5-(2,3-dihydroxypropyl)amino-1-(2-hydroxy-4-aminophenyl)benzene; 2-amino-5-(2,3-dihydroxypropyl)amino-1-(2-hydroxy-5-aminophenyl)benzene; 2-amino-5-(2,3-dihydroxypropyl)amino-1-(2-hydroxyphenyl)benzene; 2-amino-5-(2,3-dihydroxypropyl)-1-(2-methoxyphenyl)benzene; 2-amino-5-(2,3-dihydroxypropyl)amino-1-(2-methylphenyl)benzene; 2-amino-5-(2,3-dihydroxypropyl)-amino-1-(3,5-diaminophenyl)benzene; 2-amino-5-(2,3-dihydroxypropyl)amino-1-(3,5-dihydroxy-phenyl)benzene; 2-amino-5-(2,3-dihydroxypropyl)amino-1-(3-aminophenyl)benzene; 2-amino-5-(2,3-dihydroxypropyl)amino-1-(3-hydroxy-5-aminophenyl)-benzene; 2-amino-5-(2,3-dihydroxypropyl)amino-1-(3-hydroxyphenyl)benzene; 2-amino-5-(2,3-dihydroxypropyl)amino-1-(3-methoxyphenyl)benzene; 2,5-diamino-1-(3-nitrophenyl)benzene; 2-amino-5-(2,3-dihydroxypropyl)amino-1-[4-dimethylamino)phenyl]benzene; 2-amino-5-(2,3-dihydroxypropyl)amino-1-[4-(trifluoromethyl)phenyl]benzene; 2-amino-5-(2,3-dihydroxypropyl)amino-1-(4-aminophenyl)benzene; 2-amino-5-(2,3-dihydroxypropyl)amino-1-(4-carboxyphenyl)benzene; 2-amino-5-(2,3-dihydroxypropyl)amino-1-(4-carboxyphenyl)benzene; 2-amino-5-(2,3-dihydroxypropyl)amino-1-(4-hydroxyphenyl)benzene; 2-amino-5-(2,3-dihydroxypropyl)amino-1-(4-methoxyphenyl)benzene; 2-amino-5-(2,3-dihydroxypropyl)amino-1-(4-methylphenyl)benzene; 2-amino-5-(2-hydroxyethyl)amino-1-(2,3,4-trimethoxyphenyl)benzene; 2-amino-5-(2-hydroxyethyl)amino-1-(2,4-diaminophenyl)benzene; 2-amino-5-(2-hydroxyethyl)amino-1-(2,4-dihydroxyphenyl)benzene; 2-amino-5-(2-hydroxyethyl)amino-1-(2,5-diaminophenyl)benzene; 2-amino-5-(2-hydroxyethyl)amino-1-(2,5-dimethoxyphenyl)benzene; 2-amino-5-(2-hydroxyethyl)amino-1-(2,6-dimethoxyphenyl)benzene; 2-amino-5-(2-hydroxyethyl)amino-1-(2-amino-5-hydroxyphenyl)benzene; 2-amino-5-(2-hydroxyethyl)amino-1-(2-aminophenyl)benzene; 2-amino-5-(2-hydroxyethyl(amino-1-(2-hydroxy-4-aminophenyl)benzene; 2-amino-5-(2-hydroxyethyl)amino-1-(2-hydroxy-5-aminophenyl)benzene; 2-amino-5-(2-hydroxyethyl)amino-1-(2-hydroxyphenyl)benzene; 2-amino-5-(2-hydroxyethyl)amino-1-(2-hydroxyphenyl)benzene; 2-amino-5-(2-hydroxyethyl)amino-1-(2-methylphenyl)benzene; 2-amino-5-(2-hydroxyethyl)amino-1-(3,5-diaminophenyl)benzene; 2-amino-5-(2-hydroxyethyl)amino-1-(3,5-dihydroxyphenyl)benzene 2-amino-5-(2-hydroxyethyl)amino-1-(3-aminophenyl)benzene; 2-amino-5-(2-hydroxyethyl)amino-1-(3-hydroxy-5-aminophenyl)benzene; 2-amino-5-(2-hydroxyethyl)amino-1-(3-hydroxyphenyl)benzene; 2-amino-5-(2-hydroxyethyl)amino-1-(3-methoxyphenyl)benzene; 2-amino-5-(2-hydroxyethyl)amino-1-[4-(dimethylamino)phenyl]benzene; 2-amino-5-(2-hydroxyethyl)amino-1-[4-(trifluoromethyl)phenyl]benzene; 2-amino-5-(2-hydroxyethyl)amino-1-(4-aminophenyl)benzene; 2-amino-5-(2-hydroxyethyl)amino-1-(4-carboxyphenyl)benzene; 2-amino-5-(2-hydroxyethyl)amino-1-(4-chlorophenyl)benzene; 2-amino-5-(2-hydroxyethyl)amino-1-(4-hydroxyphenyl)benzene; 2-amino-5-(2-hydroxyethyl)amino-1-(4-methoxyphenyl)benzene; 2-amino-5-(2-hydroxyethyl)amino-1-(4-methylphenyl)benzene; 2-amino-5-(2-hydroxyethyl)amino-1-phenylbenzene; 2-amino-5-(2-methoxyethyl)amino-1-(2,3,4-trimethoxyphenyl)benzene; 2-amino-5-(2-methoxyethyl)amino-1-(2,4-diaminophenyl)benzene; 2-amino-5-(2-methoxyethyl)amino-1-(2,4-dihydroxyphenyl)benzene; 2-amino-5-(2-methoxyethyl)amino-1-(2,5-diaminophenyl)benzene; 2-amino-5-(2-methoxyethyl)amino-1-(2,5-dimethoxyphenyl)benzene; 2-amino-5-(2-methoxyethyl)amino-1-(2,6-dimethoxyphenyl)benzene; 2-amino-5-(2-methoxyethyl)amino-1-(2-amino-5-hydroxyphenyl)benzene; 2-amino-5-(2-methoxyethyl)amino-1-(2-aminophenyl)benzene; 2-amino-5-(2-methoxyethyl)amino-1-(2-hydroxy-4-aminophenyl)benzene; 2-amino-5-(2-methoxyethyl)amino-1-(2-hydroxy-5-aminophenyl)-benzene; 2-amino-5-(2-methoxyethyl)amino-1-(2-hydroxyphenyl)benzene; 2-amino-5-(2-methoxyethyl)amino-1-(2-methoxyphenyl)benzene; 2-amino-5-(2-methoxyethyl)amino-1-(2-methylphenyl)benzene; 2-amino-5-(2-methoxyethyl)amino-1-(3,5-diaminophenyl)benzene; 2-amino-5-(2-methoxyethyl)amino-1-(3,5-dihydroxyphenyl)benzene; 2-amino-5-(2-methoxyethyl)amino-1-(3-aminophenyl)benzene; 2-amino-5-(2-methoxyethyl)amino-1-(3-hydroxy-5-aminophenyl)benzene; 2-amino-5-(2-methoxyethyl)amino-1-(2-hydroxyphenyl)benzene; 2-amino-5-(2-methoxyethyl)amino-1-(3-methoxyphenyl)benzene; 2-amino-5-(2-methoxyethyl)amino-1-[4-(dimethylamino)phenyl])benzene; 2-amino-5-(2-methoxyethyl)amino-1-[4-(trifluoromethyl)phenyl])benzene; 2-amino-5-(2-methoxyethyl)amino-1-(4-aminophenyl)benzene; 2-amino-5-(2-methoxyethyl)amino-1-(4-carboxyphenyl)benzene; 2-amino-5-(2-methoxyethyl)amino-1-(4-chlorophenyl)benzene; 2-amino-5-(2-methoxyethyl)amino-1-(4- chlorophenyl)benzene; 2-amino-5-(2-methoxyethyl)amino-1-(4-methoxyphenyl)benzene; 2-amino-5-(2-methoxyethyl)amino-1-(4-methylphenyl)benzene; 2-amino-5-(2-methoxyethyl)amino-1-(4-methylphenyl)benzene; 2-amino-5-(2-m2methoxyethyl)amino-1-phenylbenzene; -amino-5-di-(2-hydroxyethyl)amino-1-(2,3,4-trimethoxyphenyl)benzene; 2-amino-5-di-(2-hydroxyethyl)amino-1-(2,3-difluorophenyl)benzene; 2-amino-5-di-(2-hydroxyethyl)amino-1-(2,4,6-trimethylphenyl)benzene; 2-amino-5-di-(2-hydroxyethyl)amino-1-(2,4-diaminophenyl)benzene; 2-amino-5-di-(2-hydroxyethyl)amino-1-(2,4-dichlorophenyl)benzene; 2-amino-5-di-(2-hydroxyethyl)amino-1-(2,4-dihydroxyphenyl)benzene; 2-amino-5-di-(2-hydroxyethyl)amino-1-(2,5-diaminophenyl)benzene; 2-amino-5-di-(2-hydroxyethyl)amino-1-(2,5-dimethoxyphenyl)benzene; 2-amino-5-di-(2-hydroxyethyl)amino-1-(2,6-difluorophenyl)benzene; 2-amino-5-di-(2-hydroxyethyl)amino-1-(2,6-dimethoxyphenyl)benzene; 2-amino-5-di-(2-hydroxyethyl)amino-1-(2-[(bis(1-methylethyl)amino)carbonyl]phenyl)benzene; 2-amino-5-di-(2-hydroxyethyl)amino-1-(2-[(bis(1-methylethyl)amino)carbonyl]-3-methoxyphenyl)benzene; 2-amino-5-di-(2-hydroxyethyl)-amino-1-(2-(bromomethyl)phenyl)benzene; 2-amino-5-di-(2-hydroxyethyl)amino-1-[2-(diethylamino)carbonyl]phenyl)benzene; 2-amino-5-di-(2-hydroxyethyl)amino-1-(2-amino-5-hydroxy-phenyl)benzene; 2-amino-5-di-(2-hydroxyethyl)amino-1-(2-amino phenyl)benzene; 2-amino-5-di-(2-hydroxyethyl)amino-1-(2-carboxyphenyl)benzene; 2-amino-5-di-(2-hydroxyethyl)amino-1-(2-chlorophenyl)benzene; 2-amino-5-di-(2-hydroxyethyl)amino-1-(2-fluorophenyl)benzene; 2-amino-5-di-(2-hydroxyethyl)amino-1-(2-formyl-4-methoxyphenyl)benzene; 2-amino-5-di-(2-hydroxyethyl)amino-1-(2-formyl-4-methylphenyl)benzene; 2-amino-5-di-(2-hydroxyethyl)amino-1-(2-formyl-5-methoxy-phenyl)benzene; 2-amino-5-di-(2-hydroxyethyl)amino-1-(2-formylphenyl)benzene; 2-amino-5-di-(2-hydroxyethyl)amino-1-(2-hydroxy-4-aminophenyl)benzene; 2-amino-5-di-(2-hydroxyethyl)amino-1-(2-hydroxy-5-aminophenyl)benzene; 2-amino-5-di-(2-hydroxyethyl)amino-1-(2-hydroxyphenyl)benzene; 2-amino-5-di-(2-hydroxyethyl)amino-1-(2-methoxyphenyl)benzene; 2-amino-5-di-(2-hydroxyethyl)amino-1-(2-methylphenyl)benzene; 2-amino-5-di-(2-hydroxyethyl)amino-1-(2-nitrophenyl)benzene; 2-amino-5-di-(2-hydroxyethyl)amino-1-(2-trifluoromethylphenyl)benzene; 2-amino-5-di-(2-hydroxyethyl)amino-1-(3,4-dichlorophenyl)benzene; 2-amino-5-di-(2-hydroxyethyl)amino-1-(3,5-diaminophenyl)benzene; 2-amino-5-di-(2-hydroxyethyl)amino-1-(3,5-dichlorophenyl)benzene; 2-amino-5-di-(2-hydroxyethyl)amino-1-(3,5-dihydroxyphenyl)benzene; 2-amino-5-di-(2-hydroxyethyl)amino-1-(3-acetylaminophenyl)benzene; 2-amino-5-di-(2-hydroxyethyl)amino-1-(3-aminophenyl)benzene; 2-amino-5-di-(2-hydroxyethyl)amino-1-(3-bromophenyl)benzene; 2-amino-5-di-(2-hydroxyethyl)amino-1-(3-carboxyphenyl)benzene; 2-amino-5-di-(2-hydroxyethyl)amino-1-(3-chloro-4-fluorophenyl)benzene; 2-amino-5-di-(2-hydroxyethyl)amino-1-(3-chlorophenyl)benzene; 2-amino-5-di-(2-hydroxyethyl)amino-1-(3-fluorophenyl)benzene; 2-amino-5-di-(2-hydroxyethyl)amino-1-(3-formylphenyl)benzene; 2-amino-5-di-(2-hydroxyethyl)amino-1-(3-hydroxy-5-aminophenyl)benzene; 2-amino-5-di-(2-hydroxyethyl)amino-1-(3-hydroxyphenyl)benzene; 2-amino-5-di-(2-hydroxyethyl)amino-1-(3-methoxyphenyl)benzene; 2-amino-5-di-(2-hydroxyethyl)amino-1-(3-methylphenyl)benzene; 2-amino-5-di-(2-hydroxyethyl)amino-1-(3-nitrophenyl)benzene; 2-amino-5-di-(2-hydroxyethyl)amino-1-(3-trifluoromethylphenyl)benzene; 2-amino-5-di-(2-hydroxyethyl)amino-1-[4-(bromomethyl)phenyl]benzene; 2-amino-5-di-(2-hydroxyethyl)amino-1-[4-(dimethylamino)phenyl]benzene; 2-amino-5-di-(2-hydroxyethyl)amino-1-[4-(hydroxymethyl)phenyl]benzene; 2-amino-5-di-(2-hydroxyethyl)amino-1-[4-(methylthio)phenyl]benzene; 2-amino-5-di-(2-hydroxyethyl)amino-1-[4-(trifluoromethyl)phenyl]benzene; 2-amino-5-di-(2-hydroxyethyl)amino-1-[4-(trimethylsilyl)phenyl]benzene; 2-amino-5-di-(2-hydroxyethyl)amino-1-(4-acetylphenyl)benzene; 2-amino-5-di-(2-hydroxyethyl)amino-1-(4-aminophenyl)benzene; 2-amino-5-di-(2-hydroxyethyl)amino-1-(4-bromophenyl)benzene; 2-amino-5-di-(2-hydroxyethyl)amino-1-(4-carboxyphenyl)benzene; 2-amino-5-di-(2-hydroxyethyl)amino-1-(4-chloro-3-methoxyphenyl)benzene; 2-amino-5-di-(2-hydroxyethyl)amino-1-(4-chlorophenyl)benzene; 2-amino-5-di-(2-hydroxyethyl)amino-1-(4-ethenylphenyl)benzene; 2-amino-5-di-(2-hydroxyethyl)amino-1-(4-fluorophenyl)benzene; 2-amino-5-di-(2-hydroxyethyl)amino-1-(4-formylphenyl)benzene; 2-amino-5-di-(2-hydroxyethyl)amino-1-(4-hydroxyphenyl)benzene; 2-amino-5-di-(2-hydroxyethyl)amino-1-(4-iodophenyl)benzene; 2-amino-5-di-(2-hydroxyethyl)amino-1-(4-methoxyphenyl)benzene; 2-amino-5-di-(2-hydroxyethyl)amino-1-(4-methyl-3-nitrophenyl)benzene; 2-amino-5-di-(2-hydroxyethyl)amino-1-(4-methylphenyl)benzene; 2-amino-5-di-(2-hydroxyethyl)amino-1-(5-bromo-2-methoxyphenyl)benzene; 2-amino-5-di-(2-hydroxyethyl)amino-1-chloro-2-methoxyphenyl)benzene; 2-amino-5-di-(2-hydroxyethyl)amino-1-(5-formyl-2-methoxyphenyl)benzene; 2-amino-5-di-(2-hydroxyethyl)amino-1-phenylbenzene; 2-amino-5-di-(2-methoxyethyl)amino-1-(2,3,4-trimethoxyphenyl)benzene; 2-amino-5-di-(2-methoxyethyl)amino-1-(2,3-difluoro-4-heptylphenyl)benzene; 2-amino-5-di-(2-methoxyethyl)amino-1-(2,3-difluorophenyl)benzene; 2-amino-5-di-(2-methoxyethyl)amino-1-(2,4,6-trimethylphenyl)benzene; 2-amino-5-di-(2-methoxyethyl)amino-1-(2,4-diaminophenyl)benzene; 2-amino-5-di-(2-methoxyethyl)amino-1-(2,4-dichlorophenyl)benzene; 2-amino-5-di-(2-methoxyethyl)-amino-1-(2,4-dihydroxyphenyl)benzene; 2-amino-5-di-(2-methoxyethyl)amino-1-(2,5-dimethoxyphenyl)benzene; 2-amino-5-di-(2-methoxyethyl)amino-1-(2,6-difluorophenyl)benzene; 2-amino-5-di-(2-methoxyethyl)amino-1-(2,6-dimethoxyphenyl)benzene; 2-amino-5-di-(2-methoxyethyl)amino-1-(2-[(bis(1-methylethylaminocarbonyl)phenyl]benzene; 2-amino-5-di-(2-methoxyethyl)amino-1-(2-bromomethylphenyl)benzene; 2-amino-5-di-(2-methoxyethyl)amino-1-(2-(diethylaminocarbonylphenyl)benzene; 2-amino-5-di-(2-methoxyethyl)amino-1-(2-carboxyphenyl)benzene; 2-amino-5-di-(2-methoxyethyl)amino-1-(2-chlorophenyl)benzene; 2-amino-5-di-(2-methoxyethyl)amino-1-(2-fluorophenyl)benzene; 2-amino-5-di-(2-methoxyethyl)amino-1-(2-formyl-4-methoxyphenyl)benzene; 2-amino-5-di-(2-methoxyethyl)amino-1-(2-formyl-4-methoxyphenyl)benzene; 2-amino-5-di-(2-methoxyethyl)amino-1-(2-formyl-5-methoxyphenyl)benzene; 2-amino-5-di-(2-methoxyethyl)amino-1-(2-formylphenyl)benzene; 2-amino-5-di-(2-methoxyethyl)amino-1-(2-formylphenyl)benzene; 2-amino-5-di-(2-methoxyethyl)amino-1-(2-hydroxyphenyl)benzene; 2-amino-5-di-(2-methoxyethyl)amino-1-(2-methoxyphenyl)benzene; 2-amino-5-di-(2-methoxyethyl)amino-1-(2-methoxyphenyl)benzene; 2-amino-5-di-(2-methoxyethyl)amino-1-(2-nitrophenyl)benzene; 2-amino-5-di-(2- methoxyethyl)amino-1-(2-trifluoromethylphenyl)benzene; 2-amino-5-di-(2-methoxyethyl)amino-1-(3,4-dichlorophenyl)benzene; 2-amino-5-di-(2-methoxyethyl)amino-1-(3,5-diaminophenyl)benzene; 2-amino-5-di-(2-methoxyethyl)amino-1-(3,5-dichlorophenyl)benzene; 2-amino-5-di-(2-methoxyethyl)amino-1-(3,5-dihydroxyphenyl)benzene; 2-amino-5-di-(2-methoxyethyl)amino-1-[3-(acetylamino)phenyl]benzene; 2-amino-5-di-(2-methoxyethyl)amino-1-(3-aminophenyl)benzene; 2-amino-5-di-(2-methoxyethyl)amino-1-[3-bromophenyl]benzene; 2-amino-5-di-(2-methoxyethyl)amino-1-[3-carboxyphenyl]benzene; 2-amino-5-di-(2-methoxyethyl)amino-1-[3-chloro-4-fluorophenyl]benzene; 2-amino-5-di-(2-methoxyethyl)amino-1-[3-chlorophenyl]benzene; 2-amino-5-di-(2-methoxyethyl)amino-1-[3-fluorophenyl]benzene; 2-amino-5-di-(2-methoxyethyl)amino-1-[3-formylphenyl]benzene; 2-amino-5-di-(2-methoxyethyl)amino-1-(3-hydroxyphenyl)benzene; 2-amino-5-di-(2-methoxyethyl)amino-1-(3-methoxyphenyl)benzene; 2-amino-5-di-(2-methoxyethyl)amino-1-(3-methylphenyl)benzene; 2-amino-5-di-(2-methoxyethyl)amino-1-(3-nitrophenyl)benzene; 2-amino-5-di-(2-methoxyethyl)amino-1-(3-trifluoromethylphenyl)benzene; 2-amino-5-di-(2-methoxyethyl)amino-1-(4-bromomethylphenyl)benzene; 2-amino-5-di-(2-methoxyethyl)amino-1-(4-dimethylaminophenyl)benzene; 2-amino-5-di-(2-methoxyethyl)amino-1-(4-hydroxymethylphenyl)benzene; 2-amino-5-di-(2-methoxyethyl)amino-1-(4-methylthiophenyl)benzene; 2-amino-5-di-(2-methoxyethyl)amino-1-(4-trifluoromethylphenyl)benzene; 2-amino-5-di-(2-methoxyethyl)amino-1-(4-trimethylsilylphenyl)benzene; 2-amino-5-di-(2-methoxyethyl)amino-1-(4-acetylphenyl)benzene; 2-amino-5-di-(2-methoxyethyl)amino-1-(4-aminophenyl)benzene; 2-amino-5-di-(2-methoxyethyl)amino-1-(4-carboxyphenyl)benzene; 2-amino-5-di-(2-methoxyethyl)amino-1-(4-chloro-3-methoxyphenyl)benzene; 2-amino-5-di-(2-methoxyethyl)amino-1-(4-chlorophenyl)benzene; 2-amino-5-di-(2-methoxyethyl)amino-1-(4-ethoxyphenyl)benzene; 2-amino-5-di-(2-methoxyethyl)amino-1-(4-ethoxyphenyl)benzene; 2-amino-5-di-(2-methoxyethyl)amino-1-(4-fluorophenyl)benzene; 2-amino-5-di-(2-methoxyethyl)amino-1-(4-formylphenyl)benzene; 2-amino-5-di-(2-methoxyethyl)amino-1-(4-hydroxyphenyl)benzene; 2-amino-5-di-(2-methoxyethyl)amino-1-(4-iodophenyl)benzene; 2-amino-5-di-(2-methoxyethyl)amino-1-(4-methoxyphenyl)benzene; 2-amino-5-di-(2-methoxyethyl)amino-1-(4-methyl-3-nitrophenyl)benzene; 2-amino-5-di-(2-methoxyethyl)amino-1-(4-methylphenyl)benzene; 2-amino-5-di-(2-methoxyethyl)amino-1-(5-brono-2-methoxyphenyl)benzene; 2-amino-5-di-(2-methoxyethyl)amino-1-(5-chloro-2-methoxyphenyl)benzene; 2-amino-5-di-(2-methoxyethyl)amino-1-(5-formyl-2-methoxyphenyl)benzene; 2-amino-5-dimethylamino-1-phenylbenzene; 2-amino-5-methyl-amino-1-(2,3,4-trimethoxy-phenyl)benzene; 2-amino-5-methylamino-1-(2,4-diaminophenyl)benzene; 2-amino-5-methylamino-1-(2,4-dihydroxyphenyl)benzene; 2-amino-5-methylamino-1-(2,5-diaminophenyl)benzene; 2-amino-5-methylamino-1-(2,5-dimethoxyphenyl)benzene; 2-amino-5-methylamino-1-(2,6-dimethoxyphenyl)benzene; 2-amino-5-methylamino-1-(2-amino-5-hydroxyphenyl)benzene; 2-amino-5-methylamino-1-(2-aminophenyl)benzene; 2-amino-5-methylamino-1-(2-hydroxy-4-aminophenyl)benzene; 2-amino-5-methylamino-1-(2-hydroxy-5-aminophenyl)benzene; 2-amino-5-methylamino-1-(2-hydroxyphenyl)benzene; 2-amino-5-methylamino-1-(2-methoxyphenyl)benzene; 2-amino-5-methylamino-1-(2-methylphenyl)benzene; 2-amino-5-methylamino-1-(3,5-diaminophenyl)benzene; 2-amino-5-methylamino-1-(3,5-dihydroxyphenyl)benzene; 2-amino-5-methylamino-1-(3-aminophenyl)bezene; 2-amino-5-methylamino-1-(3-hydroxy-5-aminophenyl)benzene; 2-amino-5-methylamino-1-(3-hydroxyphenyl)benzene; 2-amino-5-methylamino-1-(3-methoxyphenyl)benzene; 2-amino-5-methylamino-1-(4-dimethylaminophenyl)benzene; 2-amino-5-methylamino-1-(4-trifluoromethylphenyl)benzene; 2-amino-5-methylamino-1-(4-carboxyphenyl)benzene; 2-amino-5-methylamino-1-(4-chlorophenyl)benzene; 2-amino-5-methylamino-1-(4-hydroxyphenyl)benzene; 2-amino-5-methylamino-1-(4-methoxyphenyl)benzene; 2-amino-5-methylamino-1-(4-methylphenyl)benzene; 2-amino-5-methylamino-1-phenylbenzene; 5-amino-2-(2,3-dihydroxypropyl)amino-1-(4-bromophenyl)benzene; 5-amino-2-(2,3-dihydroxypropyl)amino-1-(4-ethenylphenyl)benzene; 5-amino-2-(2,3-dihydroxypropyl)amino-1-(2,3,4-trimethoxyphenyl)benzene; 5-amino-2-(2,3-dihydroxypropyl)amino-1-[2,4-di-(2-hydroxyethyl)aminophenyl]benzene; 5-amino-2-(2,3-dihydroxypropyl)amino-1-(2,4-diaminophenyl)benzene; 5-amino-2-(2,3-dihydroxypropyl)amino-1-(2,4-dihydroaminophenyl)benzene; 5-amino-2-(2,3-dihydroxypropyl)amino-1-(2,4-dimethylaminophenyl)benzene; 5-amino-2-(2,3-dihydroxypropyl)amino-1-(2,4-di-methoxyphenyl)benzene; 5-amino-2-(2,3-dihydroxypropyl)amino-1-[2,5-di-(2-hydroxyethyl)aminophenyl]benzene; 5-amino-2-(2,3-dihydroxypropyl)amino-1-(2,5-dimethoxyphenyl)benzene; 5-amino-2-(2,3-dihydroxypropyl)amino-1-(2,5-dihydroxyphenyl)benzene; 5-amino-2-(2,3-dihydroxypropyl)amino-1-(2,5-diaminophenyl)benzene; 5-amino-2-(2,3-dihydroxypropyl)amino-1-(2,5-dimethylaminophenyl)benzene; 5-amino-2-(2,3-dihydroxypropyl)amino-1-[2,6-di-(2-hydroxyethyl)aminophenyl]benzene; 5-amino-2-(2,3-dihydroxypropyl)amino-1-[2,6-di-aminophenyl]benzene; 5-amino-2-(2,3-dihydroxypropyl)amino-1-(2,6-dihydroxyphenyl)benzene; 5-amino-2-(2,3-dihydroxypropyl)amino-1-(2,6-dimethoxyphenyl]benzene; 5-amino-2-(2,3-dihydroxypropyl)amino-1-(2,6-dimethylaminophenyl]benzene; 5-amino-2-(2,3-dihydroxypropyl)amino-1-(2-bromomethylphenyl)benzene; 5-amino-2-(2,3-dihydroxypropyl)amino-1-(2-amino-5-hydroxyphenyl)benzene; 5-amino-2-(2,3-dihydroxypropyl)amino-1-(2-amino-5-hydroxyphenyl)benzene; 5-amino-2-(2,3-dihydroxypropyl)amino-1-(2-aminophenyl)benzene; 5-amino-2-(2,3-dihydroxypropyl)amino-1-(2-carboxyphenyl)benzene; 5-amino-2-(2,3-dihydroxypropyl)amino-1-(2-chlorophenyl)benzene; 5-amino-2-(2,3-dihydroxypropyl)amino-1[di-(2-hydroxyethyl)aminophenyl]benzene; 5-amino-2-(2,3-dihydroxypropyl)amino-1-(2-dimethylaminophenyl)benzene; 5-amino-2-(2,3-dihydroxypropyl)amino-1-(2-fluorophenyl)benzene; 5-amino-2-(2,3-dihydroxypropyl)amino-1-(2-formylphenyl)benzene; 5-amino-2-(2,3-dihydroxypropyl)amino-1-(2-hydroxy-4-aminophenyl]benzene; 5-amino-2-(2,3-dihydroxypropyl)amino-1-(2-hydroxy-5-aminophenyl)benzene; 5-amino-2-(2,3-dihydroxypropyl)amino-1-(2-hydroxyphenyl)benzene; 5-amino-2-(2,3-dihydroxypropyl)amino-1-(2-methoxyphenyl)benzene; 5-amino-2-(2,3-dihydroxypropyl)amino-1-(2-methylphenyl)benzene; 5-amino-2-(2,3-dihydroxypropyl)amino-1-(2-nitrophenyl)benzene; 5-amino-2-(2,3-dihydroxypropyl)amino-1-(2-trifluoromethylphenyl)benzene; 5-amino-2-(2,3-dihydroxypropyl)amino-1-[3,5-di-(2-hydroxyethyl)

aminophenyl]benzene; 5-amino-2-(2,3-dihydroxypropyl)amino-1-(3,5-diaminophenyl)benzene; 5-amino-2-(2,3-dihydroxypropyl)amino-1-(3,5-dihydroxyphenyl)benzene; 5-amino-2-(2,3-dihydroxypropyl)amino-1-(3,5-dimethoxyphenyl)benzene; 5-amino-2-(2,3-dihydroxypropyl)amino-1-(3,5-dimethylaminophenyl)benzene; 5-amino-2-(2,3-dihydroxypropyl)amino-1-(3-aminophenyl)benzene; 5-amino-2-(2,3-dihydroxypropyl)amino-1-(3-bromophenyl)benzene; 5-amino-2-(2,3-dihydroxypropyl)amino-1-(3-carboxyphenyl)benzene; 5-amino-2-(2,3-dihydroxypropyl)amino-1-(3-chlorophenyl)benzene; 5-amino-2-(2,3-dihydroxypropyl)amino-1-[3-di-(2-hydroxyethyl)aminophenyl]benzene; 5-amino-2-(2,3-dihydroxypropyl)amino-1-(3-dimethylaminophenyl)benzene; 5-amino-2-(2,3-dihydroxypropyl)amino-1-(3-fluorophenyl)benzene; 5-amino-2-(2,3-dihydroxypropyl)amino-1-(3-formylphenyl)benzene; 5-amino-2-(2,3-dihydroxypropyl)amino-1-(3-hydroxy-5-aminophenyl)benzene; 5-amino-2-(2,3-dihydroxypropyl)amino-1-(3-hydroxyphenyl)benzene; 5-amino-2-(2,3-dihydroxypropyl)amino-1-(3-methoxyphenyl)benzene; 5-amino-2-(2,3-dihydroxypropyl)amino-1-(3-nitrophenyl)benzene; 5-amino-2-(2,3-dihydroxypropyl)amino-1-(3-trifluoromethylphenyl)benzene; 5-amino-2-(2,3-dihydroxypropyl)amino-1-(4-dimethylaminophenyl)benzene; 5-amino-2-(2,3-dihydroxypropyl)amino-1-(4-hydroxymethylphenyl)benzene; 5-amino-2-(2,3-dihydroxypropyl)amino-1-(4-methylthiophenyl)benzene; 5-amino-2-(2,3-dihydroxypropyl)amino-1-(4-trifluoromethylphenyl)benzene; 5-amino-2-(2,3-dihydroxypropyl)amino-1-(4-trimethylsilylphenyl)benzene; 5-amino-2-(2,3-dihydroxypropyl)amino-1-(4-acetylphenyl)benzene; 5-amino-2-(2,3-dihydroxypropyl)amino-1-(4-aminophenyl)benzene; 5-amino-2-(2,3-dihydroxypropyl)amino-1-(4-carboxyphenyl)benzene; 5-amino-2-(2,3-dihydroxypropyl)amino-1-(4-chlorophenyl)benzene; 5-amino-2-(2,3-dihydroxypropyl)amino-1-[4-di-(2-hydroxyethyl)aminophenyl]benzene; 5-amino-2-(2,3-dihydroxypropyl)amino-1-(4-dimethylaminophenyl)benzene; 5-amino-2-(2,3-dihydroxypropyl)amino-1-(4-ethoxyphenyl)benzene; 5-amino-2-(2,3-dihydroxypropyl)amino-1-(4-fluorophenyl)benzene; 5-amino-2-(2,3-dihydroxypropyl)amino-1-(4-formylphenyl)benzene; 5-amino-2-(2,3-dihydroxypropyl)amino-1-(4-hydroxyphenyl)benzene; 5-amino-2-(2,3-dihydroxypropyl)amino-1-(4-methoxyphenyl)benzene; 5-amino-2-(2,3-dihydroxypropyl)amino-1-(4-methylphenyl)benzene; 5-amino-2-(2,3-dihydroxypropyl)amino-1-phenylbenzene; 5-amino-2-(2-hydroxyethyl)amino-1-(4-bromophenyl)benzene; 5-amino-2-(2-hydroxyethyl)amino-1-(4-ethenyl)benzene; 5-amino-2-(2-hydroxyethyl)amino-1-(2,3,4-trimethoxyphenyl)benzene; 5-amino-2-(2-hydroxyethyl)amino-1-[2,4-di-(2-hydroxyethyl)aminophenyl]benzene; 5-amino-2-(2-hydroxyethyl)amino-1-(2,4-diaminophenyl)benzene; 5-amino-2-(2-hydroxyethyl)amino-1-(2,4-dihydroxyphenyl)benzene; 5-amino-2-(2-hydroxyethyl)amino-1-(2,4-dimethylaminophenyl)benzene; 5-amino-2-(2-hydroxyethyl)amino-1-(2,4-dimethoxyphenyl)benzene; 5-amino-2-(2-hydroxyethyl)amino-1-[2,5-di-(2-hydroxyethyl(aminophenyl]benzene; 5-amino-2-(2-hydroxyethyl)amino-1-(2,5-diaminophenyl)benzene; 5-amino-2-(2-hydroxyethyl)amino-1-(2,5-dihydroxyphenyl)benzene; 5-amino-2-(2-hydroxyethyl)amino-1-(2,5-dimethoxyphenyl)benzene; 5-amino-2-(2-hydroxyethyl)amino-1-(2,5-dimethylaminophenyl)benzene; 5-amino-2-(2-hydroxyethyl)amino-1-[2,6-di-(2-hydroxyethyl(aminophenyl]benzene; 5-amino-2-(2-hydroxyethyl)amino-1-(2,6-diaminophenyl)benzene; 5-amino-2-(2-hydroxyethyl)amino-1-(2,6-dihydroxyphenyl)benzene; 5-amino-2-(2-hydroxyethyl)amino-(2,6-dimethoxyphenyl)benzene; 5-amino-2-(2-hydroxyethyl)amino-1-(2,6-dimethylaminophenyl)benzene; 5-amino-2-(2-hydroxyethyl)amino-1-(2-bromomethylphenyl)benzene; 5-amino-2-(2-hydroxyethyl)amino-1-(2-amino-5-hydroxyphenyl)benzene; 5-amino-2-(2-hydroxyethyl)amino-1-(2-aminophenyl)benzene; 5-amino-2-(2-hydroxyethyl)amino-1-(2-carboxyphenyl)benzene; 5-amino-2-(2-hydroxyethyl)amino-1-(2-chlorophenyl)benzene; 5-amino-2-(2-hydroxyethyl)amino-1-[2-di-(2-hydroxyethyl)aminophenyl]benzene; 5-amino-2-(2-hydroxyethyl)amino-1-(2-dimethylaminophenyl)benzene; 5-amino-2-(2-hydroxyethyl)amino-1-(2-fluorophenyl)benzene; 5-amino-2-(2-hydroxyethyl)amino-1-(2-formylphenyl)benzene; 5-amino-2-(2-hydroxyethyl)amino-1-(2-hydroxy-4-aminophenyl)benzene; 5-amino-2-(2-hydroxyethyl)amino-1-(2-hydroxy-5-aminophenyl)benzene; 5-amino-2-(2-hydroxyethyl)amino-1-(2-hydroxyphenyl)benzene; 5-amino-2-(2-hydroxyethyl)amino-1-(2-methoxyphenyl)benzene; 5-amino-2-(2-hydroxyethyl)amino-1-(2-methylphenyl)benzene; 5-amino-2-(2-hydroxyethyl)amino-1-(2-nitrophenyl)benzene; 5-amino-2-(2-hydroxyethyl)amino-1-(2-trifluoromethylphenyl)benzene; 5-amino-2-(2-hydroxyethyl)amino-1-[3,5-di-(2-hydroxyethyl)aminophenyl]benzene; 5-amino-2-(2-hydroxyethyl)amino-1-(3,5-diaminophenyl)benzene; 5-amino-2-(2-hydroxyethyl)amino-1-(3,5-dihydroxyphenyl)benzene; 5-amino-2-(2-hydroxyethyl)amino-1-(3,5-dimethoxyphenyl)benzene; 5-amino-2-(2-hydroxyethyl)amino-1-(3,5-dimethylaminophenyl)benzene; 5-amino-2-(2-hydroxyethyl)amino-1-(3-aminophenyl)benzene; 5-amino-2-(2-hydroxyethyl)amino-1-(3-bromophenyl)benzene; 5-amino-2-(2-hydroxyethyl)amino-1-(3-carboxyphenyl)benzene; 5-amino-2-(2-hydroxyethyl)amino-1-(3-chlorophenyl)benzene; 5-amino-2-(2-hydroxyethyl)amino-1-[3-(di-(2-hydroxyethyl)aminophenyl]benzene; 5-amino-2-(2-hydroxyethyl)amino-1-(3-dimethylaminophenyl)benzene; 5-amino-2-(2-hydroxyethyl)amino-1-(3-fluorophenyl)benzene; 5-amino-2-(2-hydroxyethyl)amino-1-(3-formylphenyl)benzene; 5-amino-2-(2-hydroxyethyl)amino-1-(3-hydroxy-5-aminophenyl)benzene; 5-amino-2-(2-hydroxyethyl(amino-1-(3-hydroxyphenyl)benzene; 5-amino-2-(2-hydroxyethyl)amino-1-(3-methoxyphenyl)benzene; 5-amino-2-(2-hydroxyethyl)amino-1-(3-nitrophenyl)benzene; 5-amino-2-(2-hydroxyethyl)amino-1-(3-trifluoromethylphenyl)benzene; 5-amino-2-(2-hydroxyethyl)amino-1-[4-(dimethylamino)phenyl]benzene; 5-amino-2-(2-hydroxyethyl)amino-1-[4-hydroxymethyl)phenyl]benzene; 5-amino-2-(2-hydroxyethyl)amino-1-[4-(methylthio)phenyl]benzene; 5-amino-2-(2-hydroxyethyl)amino-1-[4-(trifluoromethyl) phenyl]benzene; 5-amino-2-(2-hydroxyethyl)amino-1-[4-(trimethylsilyl)phenyl]benzene; 5-amino-2-(2-hydroxyethyl)amino-1-(4-acetylphenyl)benzene; 5-amino-2-(2-hydroxyethyl)amino-1-(4-aminophenyl)benzene; 5-amino-2-(2-hydroxyethyl)amino-1-(4-carboxyphenyl)benzene; 5-amino-2-(2-hydroxyethyl)amino-1-(4-chlorophenyl)benzene; 5-amino-2-(2-hydroxyethyl)amino-1-[4-di-(2-hydroxyethyl)aminophenyl]benzene; 5-amino-2-(2-hydroxyethyl)amino-1-(4-dimethylaminophenyl)benzene; 5-amino-2-(2-hydroxyethyl)amino-1-(4-ethoxyphenyl)benzene; 5-amino-2-(2-hydroxyethyl)amino-1-(4-fluorophenyl)benzene; 5-amino-2-(2-hydroxyethyl)amino-1-(4-formylphenyl)

benzene; 5-amino-2-(2-hydroxyethyl)amino-1-(4-hydroxyphenyl)benzene; 5-amino-2-(2-hydroxyethyl)amino-1-(4-methoxyphenyl)benzene; 5-amino-2-(2-hydroxyethyl)amino-1-(4-methylphenyl)benzene; 5-amino-2-(2-hydroxyethyl)amino-1-phenylbenzene; 5-amino-2-(2-methoxyethyl)amino-1-(2,3,4-trimethoxyphenyl)benzene; 5-amino-2-(2-methoxyethyl)amino-1-(2,4-diamino-phenyl)benzene; 5-amino-2-(2-methoxyethyl)amino-1-(2,4-dihydroxyphenyl)benzene; 5-amino-2-(2-methoxyethyl)amino-1-(2,5-diaminophenyl)benzene; 5-amino-2-(2-methoxyethyl)amino-1-(2,5-dimethoxyphenyl)benzene; 5-amino-2-(2-methoxyethyl)amino-1-(2,6-dimethoxyphenyl)benzene; 5-amino-2-(2-methoxyethyl)amino-1-(2-amino-5-hydroxyphenyl)benzene; 5-amino-2-(2-methoxyethyl)amino-1-(2-aminophenyl)benzene; 5-amino-2-(2-methoxyethyl)amino-1-(2-hydroxy-4-aminophenyl)benzene; 5-amino-2-(2-methoxyethyl)amino-1-(2-hydroxy-5-aminophenyl)benzene; 5-amino-2-(2-methoxyethyl)amino-1-(2-hydroxyphenyl)benzene; 5-amino-2-(2-methoxyethyl)amino-1-(2-methoxyphenyl)benzene; 5-amino-2-(2-methoxyethyl)amino-1-(2-methylphenyl)benzene; 5-amino-2-(2-methoxyethyl)amino-1-(3,5-diaminophenyl)benzene; 5-amino-2-(2-methoxyethyl)amino-1-(3,5-dihydroxyphenyl)benzene; 5-amino-2-(2-methoxyethyl)amino-1-(3-aminophenyl)benzene; 5-amino-2-(2-methoxyethyl)amino-1-(3-hydroxy-5-aminophenyl)benzene; 5-amino-2-(2-methoxyethyl)amino-1-(3-hydroxyphenyl)benzene; 5-amino-2-(2-methoxyethyl)amino-1-(3-methoxyphenyl)benzene; 5-amino-2-(2-methoxyethyl)amino-1-[4-dimethylamino)phenyl]benzene; 5-amino-2-(2-methoxyethyl)amino-1-[4-(trifluoromethyl)phenyl]benzene; 5-amino-2-(2-methoxyethyl)amino-1-(4-aminophenyl)benzene; 5-amino-2-(2-methoxyethyl)amino-1-(4-carboxyphenyl)benzene; 5-amino-2-(2-methoxyethyl)amino-1-(4-chlorophenyl)benzene; 5-amino-2-(2-methoxyethyl)amino-1-(4-hydroxyphenyl)benzene; 5-amino-2-(2-methoxyethyl)amino-1-(4-methylphenyl)benzene; 5-amino-2-(2-methoxyethyl)amino-1-(4-methylphenyl)benzene; 5-amino-2-(2-methoxyethyl)amino-1-phenylbenzene; 5-amino-2-di(2-hydroxyethyl)amino-1-(2,3,4-trimethoxyphenyl)benzene; 5-amino-2-di(2-hydroxyethyl)amino-1-(2,3-difluoro-4-heptylphenyl)benzene; 5-amino-2-di(2-hydroxyethyl)amino-1-(2,3-difluorophenyl)benzene; 5-amino-2-di(2-hydroxyethyl)amino-1-(2,4,6-trimethylphenyl)benzene; 5-amino-2-di(2-hydroxyethyl)amino-1-(2,4-diaminophenyl)benzene; 5-amino-2-di(2-hydroxyethyl)amino-1-(2,4-dichlorophenyl)benzene; 5-amino-2-di(2-hydroxyethyl)amino-1-(2,4-dihydroxyphenyl)benzene; 5-amino-2-di(2-hydroxyethyl)amino-1-(2,5-dimethoxyphenyl)benzene; 5-amino-2-di(2-hydroxyethyl)amino-1-(2,6-difluorophenyl)benzene; 5-amino-2-di(2-hydroxyethyl)amino-1-(2,6-dimethoxyphenyl)benzene; 5-amino-2-di(2-hydroxyethyl)amino-1-(2-[(bis(1-methylethyl)amino)carbonyl]phenyl]benzene; 5-amino-2-di(2-hydroxyethyl)amino-1-(2-[(bis(1-methylethyl)amino)carbonyl)-3-methoxyphenyl]benzene; 5-amino-2-di(2-hydroxyethyl)amino-1-(2-bromomethylphenyl)benzene; 5-amino-di(2-hydroxyethyl)amino-1-(2-diethylaminocarbonyl)phenyl)benzene; 5-amino-2-di(2-hydroxyethyl)amino-1-(2-carboxyphenyl)benzene; 5-amino-2-di(2-hydroxyethyl)amino-1-(2-chlorophenyl)benzene; 5-amino-2-di(2-hydroxyethyl)amino-1-(2-fluorophenyl)benzene; 5-amino-2-di(2-hydroxyethyl)amino-1-(2-formyl-4-methoxyphenyl)benzene; 5-amino-2-di(2-hydroxyethyl)amino-1-(2-formyl-4-methylphenyl)benzene; 5-amino-2-di(2-hydroxyethyl)amino-1-(2-formyl-5-methoxyphenyl)benzene; 5-amino-2-di(2-hydroxyethyl)amino-1-(2-formylphenyl)benzene; 5-amino-2-di(2-hydroxyethyl)amino-1-(2-hydroxy-4-aminophenyl)benzene; 5-amino-2-di(2-hydroxyethyl)amino-1-(2-hydroxyphenyl)benzene; 5-amino-2-di(2-hydroxyethyl)amino-1-(2-methoxyphenyl)benzene; 5-amino-2-di(2-hydroxyethyl)amino-1-(2-methylphenyl)benzene; 5-amino-2-di(2-hydroxyethyl)amino-1-(2-nitrophenyl)benzene; 5-amino-2-di(2-hydroxyethyl)amino-1-(2-trifluoromethylphenyl)benzene; 5-amino-2-di(2-hydroxyethyl)amino-1-(3,4-dichlorophenyl)benzene; 5-amino-2-di(2-hydroxyethyl)amino-1-(3,5-diaminophenyl)benzene; 5-amino-2-di(2-hydroxyethyl)amino-1-(3,5-dichlorophenyl)benzene; 5-amino-2-di(2-hydroxyethyl)amino-1-(3,5-dihydroxyphenyl)benzene; 5-amino-2-di(2-hydroxyethyl)amino-1-(3-acetylaminophenyl)benzene; 5-amino-2-di(2-hydroxyethyl)amino-1-(3-aminophenyl)benzene; 5-amino-2-di(2-hydroxyethyl)amino-1-(3-bromophenyl)benzene; 5-amino-2-di(2-hydroxyethyl)amino-1-(3-carboxyphenyl)benzene; 5-amino-2-di(2-hydroxyethyl)amino-1-(3-chloro-4-fluorophenyl)benzene; 5-amino-2-di(2-hydroxyethyl)amino-1-(3-chlorophenyl)benzene; 5-amino-2-di(2-hydroxyethyl)amino-1-(3-fluorophenyl)benzene; 5-amino-2-di(2-hydroxyethyl)amino-1-(3-formylphenyl)benzene; 5-amino-2-di(2-hydroxyethyl)amino-1-(3-hydroxyphenyl)benzene; 5-amino-2-di(2-hydroxyethyl)amino-1-(3-methoxyphenyl)benzene; 5-amino-2-di(2-hydroxyethyl)amino-1-(3-methylphenyl)benzene; 5-amino-2-di(2-hydroxyethyl)amino-1-(3-nitrophenyl)benzene; 5-amino-2-di(2-hydroxyethyl)amino-1-(3-trifluoromethylphenyl)benzene; 5-amino-2-di(2-hydroxyethyl)amino-1-(4-(bromomethylphenyl)benzene; 5-amino-2-di(2-hydroxyethyl)amino-1-(4-dimethylaminophenyl)benzene; 5-amino-2-di(2-hydroxyethyl)amino-1-(4-hydroxymethylphenyl)benzene; 5-amino-2-di(2-hydroxyethyl)amino-1-(4-methylthiophenyl)benzene; 5-amino-2-di(2-hydroxyethyl)amino-1-(4-trifluoromethylphenyl)benzene; 5-amino-2-di(2-hydroxyethyl)amino-1-(4-trimethylsilylphenyl)benzene; 5-amino-2-di(2-hydroxyethyl)amino-1-(4-acetylphenyl)benzene; 5-amino-2-di(2-hydroxyethyl)amino-1-(4-aminophenyl)benzene; 5-amino-2-di(2-hydroxyethyl)amino-1-(4-bromophenyl)benzene; 5-amino-2-di(2-hydroxyethyl)amino-1-(4-carboxyphenyl)benzene; 5-amino-2-di(2-hydroxyethyl)amino-1-(4-chloro-3-methoxyphenyl)benzene; 5-amino-2-di(2-hydroxyethyl)amino-1-(4-chlorophenyl)benzene; 5-amino-2-di(2-hydroxyethyl)amino-1-(4-ethenylphenyl)benzene; 5-amino-2-di(2-hydroxyethyl)amino-1-(4-ethoxyphenyl)benzene; 5-amino-2-di(2-hydroxyethyl)amino-1-(4-fluorophenyl)benzene; 5-amino-2-di(2-hydroxyethyl)amino-1-(4-formylphenyl)benzene; 5-amino-2-di(2-hydroxyethyl)amino-1-(4-hydroxyphenyl)benzene; 5-amino-2-di(2-hydroxyethyl)amino-1-(4-iodophenyl)benzene; 5-amino-2-di(2-hydroxyethyl)amino-1-(4-methoxyphenyl)benzene; 5-amino-2-di(2-hydroxyethyl)amino-1-(4-methyl-3-nitrophenyl)benzene; 5-amino-2-di(2-hydroxyethyl)amino-1-(4-methylphenyl)benzene; 5-amino-2-di(2-hydroxyethyl)amino-1-(5-bromo-2-methoxyphenyl)benzene; 5-amino-2-di(2-hydroxyethyl)amino-1-(5-chloro-2-methoxyphenyl)benzene; 5-amino-2-di(2-hydroxyethyl)amino-1-(5-formyl-2-methoxyphenyl)benzene; 5-amino-2-di(2-methoxyethyl)amino-1-(2,3,4-trimethoxyphenyl)benzene; 5-amino-2-di(2-methoxyethyl)amino-1-(2,3-difluoro-4-heptylphenyl)benzene; 5-amino-2-di(2-methoxyethyl)amino-1-(2,3-difluorophenyl)benzene; 5-amino-2-di(2-methoxyethyl)

amino-1-(2,4,6-trimethylphenyl)benzene; 5-amino-2-di(2-methoxyethyl)amino-1-(2,4-diaminophenyl)benzene; 5-amino-2-di(2-methoxyethyl)amino-1-(2,4-dichlorophrnyl)benzene; 5-amino-2-di(2-methoxyethyl)amino-1-(2,4-dihydroxyphenyl)benzene; 5-amino-2-di(2-methoxyethyl)amino-1-(2,5-dimethoxyphenyl)benzene; 5-amino-2-di(2-methoxyethyl)amino-1-(2,6-difluorophenyl)benzene; 5-amino-2-di(2-methoxyethyl)amino-1-(2,6-dimethoxyphenyl)benzene; 5-amino-2-di(2-methoxyethyl)amino-1-(2-[(bis(1-methylethylaminocarbonyl)phenyl]benzene; 5-amino-2-di(2-methoxyethyl)amino-1-(2-[(bis(1-methylethylaminocarbonyl)-3-methoxyphenyl]benzene; 5-amino-2-di(2-methoxyethyl)amino-1-(2-bromomethylphenyl)benzene; 5-amino-2-di(2-methoxyethyl)amino-1-[2-(diethylaminocarbonyl)phenyl]benzene; 5-amino-2-di(2-methoxyethyl)amino-1-[2-carboxyphenyl)benzene; 5-amino-2-di(2-methoxyethyl)amino-1-[2-chlorophenyl)benzene; 5-amino-2-di(2-methoxyethyl)amino-1-(2-fluorophenyl)benzene; 5-amino-2-di]-(2-methoxyethyl)amino-1-(2-formyl-4-methoxyphenyl)benzene; 5-amino-2-di(2-methoxyethyl)amino-1-(2-formyl-4-methylphenyl)benzene; 5-amino-2-di(2-methoxyethyl)amino-1-(2-formyl-5-methoxyphenyl)benzene; 5-amino-2-di(2-methoxyethyl)amino-1-(2-formylphenyl)benzene; 5-amino-2-di(2-methoxyethyl)amino-1-(2-hydroxy-4-aminophenyl)benzene; 5-amino-2-di(2-methoxyethyl)amino-1-(2-hydroxyphenyl)benzene; 5-amino-2-di(2-methoxyethyl)amino-1-(2-methoxyphenyl)benzene; 5-amino-2-di(2-methoxyethyl)amino-1-(2-methylphenyl)benzene; 5-amino-2-di(2-methoxyethyl)amino-1-(2-nitrophenyl)benzene; 5-amino-2-di(2-methoxyethyl)amino-1-(2-trifluoromethylphenyl)benzene; 5-amino-2-di(2-methoxyethyl)amino-1-(3,4-dichlorophenyl)benzene; 5-amino-2-di(2-methoxyethyl)amino-1-(3,5-diaminophenyl)benzene; 5-amino-2-di(2-methoxyethyl)amino-1-(3,5-dichlorophenyl)benzene; 5-amino-2-di(2-methoxyethyl)amino-1-(3,5-dihydroxyphenyl)benzene; 5-amino-2-di(2-methoxyethyl)amino-1-(3-acetylaminophenyl)benzene; 5-amino-2-di(2-methoxyethyl)amino-1-(3-aminophenyl)benzene; 5-amino-2-di(2-methoxyethyl)amino-1-(3-bromophenyl)benzene; 5-amino-2-di(2-methoxyethyl)amino-1-(3-carboxyphenyl)benzene; 5-amino-2-di(2-methoxyethyl)amino-1-(3-chloro-4-fluorophenyl)benzene; 5-amino-2-di(2-methoxyethyl)amino-1-(3-chlorophenyl)benzene; 5-amino-2-di(2-methoxyethyl)amino-1-(3-fluorophenyl)benzene; 5-amino-2-di(2-methoxyethyl)amino-1-(3-formylphenyl)benzene; 5-amino-2-di(2-methoxyethyl)amino-1-(3-hydroxyphenyl)benzene; 5-amino-2-di(2-methoxyethyl)amino-1-(3-methoxyphenyl)benzene; 5-amino-2-di(2-methoxyethyl)amino-1-(3-methylphenyl)benzene; 5-amino-2-di(2-methoxyethyl)amino-1-(3-nitrophenyl)benzene; 5-amino-2-di(2-methoxyethyl)amino-1-(3-trifluoromethylphenyl)benzene; 5-amino-2-di(2-methoxyethyl)amino-1-(4-bromomethylphenyl)benzene; 5-amino-2-di(2-methoxyethyl)amino-1-(4-dimethylaminophenyl)benzene; 5-amino-2-di(2-methoxyethyl)amino-1-(4-hydroxymethylphenyl)benzene; 5-amino-2-di(2-methoxyethyl)amino-1-(4-methylthiophenyl)benzene; 5-amino-2-di(2-methoxyethyl)amino-1-(4-trifluoromethylphenyl)benzene; 5-amino-2-di(2-methoxyethyl)amino-1-(4-trimethylsilylphenyl)benzene; 5-amino-2-di(2-methoxyethyl)amino-1-(4-acetylphenyl)benzene; 5-amino-2-di(2-methoxyethyl)amino-1-(4-aminiphenyl)benzene; 5-amino-2-di(2-methoxyethyl)amino-1-(4-bromophenyl)benzene; 5-amino-2-di(2-methoxyethyl)amino-1-(4-carboxyphenyl)benzene; 5-amino-2-di(2-methoxyethyl)amino-1-(4-chloro-3-methoxyphenyl)benzene; 5-amino-2-di(2-methoxyethyl)amino-1-(4-chlorophenyl)benzene; 5-amino-2-di(2-methoxyethyl)amino-1-(4-ethenylphenyl)benzene; 5-amino-2-di(2-methoxyethyl)amino-1-(4-ethoxyphenyl)benzene; 5-amino-2-di(2-methoxyethyl)amino-1-(4-formylphenyl)benzene; 5-amino-2-di(2-methoxyethyl)amino-1-(4-hydroxymethylphenyl)benzene; 5-amino-2-di(2-methoxyethyl)amino-1-(4-iodophenyl)benzene; 5-amino-2-di(2-methoxyethyl)amino-1-(4-methoxyphenyl)benzene; 5-amino-2-di(2-methoxyethyl)amino-1-(4-methyl-3-nitrophenyl)benzene; 5-amino-2-di(2-methoxyethyl)amino-1-(4-methylphenyl)benzene; 5-amino-2-di(2-methoxyethyl)amino-1-(5-bromo-2-methoxyphenyl)benzene; 5-amino-2-di(2-methoxyethyl)amino-1-(5-chloro-2-methoxyphenyl)benzene; 5-amino-2-di(2-methoxyethyl)amino-1-(5-formyl-2-methoxyphenyl)benzene; 5-amino-2-dimethylamino-1-phenylbenzene; 5-amino-2-methylamino-1-(2,3,4-trimethoxyphenyl)benzene; 5-amino-2-methylamino-1-(2,4-diaminophenyl)benzene; 5-amino-2-methylamino-1-(2,4-dihydroxyphenyl)benzene; 5-amino-2-methylamino-1-(2,5-diaminophenyl)benzene; 5-amino-2-methylamino-1-(2,5-dimethoxyphenyl)benzene; 5-amino-2-methylamino-1-(2,6-dimethoxyphenyl)benzene; 5-amino-2-methylamino-1-(2-amino-5-hydroxyphenyl)benzene; 5-amino-2-methylamino-1-(2-aminophenyl)benzene; 5-amino-2-methylamino-1-(2-hydroxy-4-aminophenyl)benzene; 5-amino-2-methylamino-1-(2-hydroxy-5-aminophenyl)benzene; 5-amino-2-methylamino-1-(2-hydroxyphenyl)benzene; 5-amino-2-methylamino-1-(2-methoxyphenyl)benzene; 5-amino-2-methylamino-1-(2-methylphenyl)benzene; 5-amino-2-methylamino-1-(3,5-diaminophenyl)benzene; 5-amino-2-methylamino-1-(3,5-dihydroxyphenyl)benzene; 5-amino-2-methylamino-1-(3-aminophenyl)benzene; 5-amino-2-methylamino-1-(3-hydroxy-5-aminophenyl)benzene; 5-amino-2-methylamino-1-(3-hydroxyphenyl)benzene; 5-amino-2-methylamino-1-(3-methoxyphenyl)benzene; 5-amino-2-methylamino-1-(4-dimethylaminophenyl)benzene; 5-amino-2-methylamino-1-(4-trifluoromethylphenyl)benzene; 5-amino-2-methylamino-1-(4-aminophenyl)benzene; 5-amino-2-methylamino-1-(4-carboxyphenyl)benzene; 5-amino-2-methylamino-1-(4-chlorophenyl)benzene; 5-amino-2-methylamino-1-(4-hydroxyphenyl)benzene; 5-amino-2-methylamino-1-(4-methoxyphenyl)benzene; 5-amino-2-methylamino-1-(4-methylphenyl)benzene and 5-amino-2-methylamino-1-phenylbenzene.

Preferred are compounds of formula (I) wherein (i) R1 and R2 or R3 and R4 or all radicals from R1 to R4 denote hydrogen and/or (ii) four of radicals R6 to R10 represent hydrogen and the fifth radical denotes hydrogen or a —C(OH)H, —C(O)CH$_3$, C$_1$–C$_4$ alkyl or C$_1$–C$_4$ hydroxyalkyl group and/or (iii) R5 denotes hydrogen.

Particularly well suited 2,5-diamino-1-phenylbenzene derivatives of formula (I) in terms of the overall invention are 2,5-diamino-1-phenylbenzene; 2,5-diamino-1-(3-nitrophenyl)benzene; 2,5-diamino-1-(4-methoxyphenyl)benzene; 2,5-diamino-1-(3-aminophenyl)benzene; 2,5-diamino-1-(2-methylphenyl)benzene; 2,5-diamino-1-(3-methylphenyl)benzene; 2,5-diamino-1-(4-methylphenyl)benzene; 2,5-diamino-1-(3-chlorophenyl)benzene and 2,5-diamino-1-(4-chlorophenyl)benzene or the physiologically tolerated salts thereof.

The compounds of formula (I) can be used as free bases or in the form of their physiologically tolerated salts with inorganic or organic acids such as, for example, hydrochloric, sulfuric, phosphoric, acetic, propionic, lactic or citric acid.

The colorants of the invention contain the 2,5-diamino-1-phenylbenzene derivative of formula (I) in an amount from about 0.005 to 20 wt %, an amount from about 0.01 to 5.0 wt % and particularly from 0.1 to 2.5 wt % being especially preferred.

Suitable couplers are preferably 2,6-diaminopyridine, 2-amino-4-[(2-hydroxyethyl)amino]anisole, 2,4-diamino-1fluoro-5-methylbenzene, 2,4-diamino-1-methoxy-5-methylbenzene, 2,4-di-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4 dichlorophenol, 3-amino-2-methylphenol, 3-amino-2-chloro-6-methylphenol, 3-aminophenol, 2-[(3-hydroxyphenyl)amino]acetaminde, 5-[(2-hydroxyethyl)amino]-2-methylphenol, 3-](2-hydroxyethyl)aminol, 3-[(2-methoxyethyl)amino]phenol, 5-amino-2-ethylphenol, 2-(4-amino-2-hydroxyphenoxy)ethanol, 5-[3-(hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylene dioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)benzoxazine, 3-methyl-1-phenyl-5-pyrazolone, 5,6-dihydroxyindo 5,6-dihydroxyindoline, 5-hydroxyindole, 6-hydroxyindole, 7-hydroxyindole and 2,3-indolinedione.

Although the advantageous properties of the diamino benzene derivatives of formula (I) suggest that said derivatives be used as the only developer, it is, of course, possible to use diaminobenzene derivatives of formula (I) together with other known developers, for example with 1,4-diaminobenzene, 2,5-diaminotoluene, 2,5-diaminophenylethyl alcohol, 4-aminophenol and its derivatives, for example 4-amino-3-methylphenol, 4,5-diamino-1-(2-hydroxyethyl)pyranole or a tetraaminopyrimidine.

In the colorant of the invention, the couplers and developers can be contained alone or in admixture with each other, the total amount of couplers and developers in the colorant of the invention ranging from 0.005 to 20 wt %, preferably from about 0.01 to 5.0 wt % and particularly from 0.1 to 2.5 wt % (based on the total amount of colorant).

The total amount of the developer-coupler combination contained in the colorants described here is preferably about 0.01 to 20 wt %, an amount from about 0.02 to 10 wt % and particularly from 0.2 to 6.0 wt % being especially preferred. In general, the developers and couplers are used in about equimolar amounts. It is not disadvantageous, however, to use the developer in a certain excess or deficiency, for example in a coupler:developer ratio of 1:2 to 1:0.5.

Moreover, the colorant of the invention can also contain other components, for example 6-amino-2-methylphenol and 2-amino-5-methylphenol, as well as common direct dyes, for example triphenylmethane dyes such as [(4'-aminophenyl)-(4'-imino-2",5"-cyclohexadien-1"-ylidene)methyl-2-methylaminobenze monohydrochloride (C.I. 42510) and 4-[(4'-amino-3'-methylphenyl)(4"-imino-3"-methyl-2",5"-cyclohexadient-1"-yl)idine)methyl]-2-methylaminobenzene monohydrochloride (C.I.42520), aromatic nitro dyes, such as 4-(2'-hydroxyethyl)aminonitrotoluene, 2-amino-4,6-dinitrophenol, 2-amino-5-(2'-hydroxyethyl)aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-[(2'-ureidoethyl)amino-4-nitrobenzene, furthermore azo dyes such as sodium 6-[(4'aminophenyl])azo]-5-hydroxynaphthalenesulfonate, and disperse dyes such as, for example 1,4-diaminoanthraquinone and 1,4,5,8-tetraaminoanthraquinone. The colorants can contain these components in an amount from about 0.1 to 4.0 wt %.

Naturally, the couplers and developers as well as the other dye components, if they are bases, can also be used in the form of their physiologically tolerated salts with organic or inorganic acids such as, for example, hydrochloric or sulfuric acid, or—if they contain aromatic OH groups—in the form of salts with bases, for example as their alkali metal phenoxides.

Moreover, the colorants, if they are intended for coloring hair, can contain other common cosmetic additives, for example antioxidants such as ascorbic acid, thioglycolic acid or sodium sulfite, as well as perfumes, complexing agents, wetting agents, emulsifiers, thickeners and hair-care agents. The form in which the colorant preparations of the invention appear can be, for example, that of a solution, particularly an aqueous or aqueous-alcoholic solution. Particularly preferred preparation forms, however, are creams, gels or emulsions. Their composition consists of a mixture of dye components and the usual additives for such preparations.

Conventional additives to solutions, creams, emulsions or gels are, for example, solvents such as water, the lower aliphatic alcohols, for example ethanol, propanol or isopropanol, glycerol or glycols such as 1,2-propylene glycol, moreover wetting agents or emulsifiers from the class of anionic, cationic, amphoteric or nonionic surfactants, such as fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty alkanolamides, ethoxylated fatty esters, furthermore thickeners, such as the fatty alcohols, starch or cellulose derivatives, furthermore vaseline, paraffin oil and fatty acids as well as hair-care agents such as cationic resins, lanolin derivatives, cholesterol, pantothenic acid and betaine. The said constituents are employed in amounts normally used for such purposes, for example the wetting agents and emulsifiers in an amount from about 0.5 to 30 wt %, the thickeners in an amount from about 0.1 to 25 wt % and the hair-care agents at a concentration of about 0.1 to 5.0 wt %.

Depending on the composition, the colorant of the invention can be weakly acidic, neutral or alkaline. In particular, it has a pH from 6.8 to 11.5, the adjustment to alkaline pH preferably being done with ammonia. Organic amines, for example monoethanolamine and triethanolamine, as well as inorganic bases such as sodium hydroxide and potassium hydroxide, however, can also be used. Suitable for pH adjustment to an acidic value are inorganic or organic acids, for example phosphoric, acetic, citric or tartaric acid.

To use the afore-described colorants for oxidative dyeing of hair, said colorants are mixed with an oxidant immediately before use, and the mixture is applied to hair in an amount sufficient for hair treatment which, depending on hair fullness, is generally from about 60 to 200 grams.

Suitable oxidants for developing the hair color are mainly hydrogen peroxide or a compound of addition of hydrogen perbxide to urea, melamine, sodium borate or sodium carbonate, in the form of a 3 to 12%, preferably 6%, aqueous solution, as well as air oxygen. When a 6% hydrogen peroxide solution is used as the oxidant, the weight ratio of hair colorant to oxidant is 5:1 to 2:1, and preferably 1:1. Larger amounts of oxidant are used primarily when the hair colorant contains a higher dye concentration or when stronger hair bleaching is desired at the same time. The mixture is allowed to act on the hair at 15 to 50° C. for about 10 to 45 minutes and preferably for 30 minutes. The hair is then rinsed with water and dried. Optionally, this rinse can be followed with a shampoo wash, optionally followed by rinsing with a weak organic acid, for example citric or tartaric acid. The hair is then dried.

The colorant of the invention containing as the developer a diaminobenzene derivative of formula (I) affords colorations of excellent color fastness, particularly in terms of light fastness, wash fastness and rubbing fastness. As regards the coloring properties, the colorants of the invention, depending on the type and composition of the dye components, provide a wide range of different color shades ranging from brown, purple, violet to blue and black shades. The color intensity of the color shades is particularly good. The very good coloring properties of the colorants of the present patent application also manifest themselves, in particular, in that these colorants make it possible readily to color with good coverage gray, chemically not predamaged hair.

The 2,5-diamino-1-phenylbenzene derivatives of formula (I) are readily water-soluble affording colorations of high color intensity and outstanding color fastness, particularly as regards light fastness, wash fastness and rubbing fastness. Moreover, they show excellent storage stability, particularly as components of the aforedescribed colorants.

Another object of the present invention are novel 2,5-diamino-1-phenylbenzene derivatives of formula (I) or the physiologically tolerated water-soluble salts thereof, water-soluble salts wherein at least one of radicals R1 to R10 is different from hydrogen.

The 2,5-diamino-1-phenylbenzene derivatives of formula (I) can be prepared by known synthetic methods, for example by the methods described in the following practical examples.

The following examples are intended to further illustrate the object of the invention without limiting it to these examples.

EXAMPLES

Example 1

Synthesis of 2,5-Diamino-1-Phenylbenzene Derivatives of Formula (I) (General Method of Synthesis)

A. Synthesis of 2,5-tert.Butylcarbonylaminobromobenzene 15.65 g (0.07 mole) of bromo-p-phenylenediamine hydrochloride and 32.7 g (0.15 mole) of ditert.butyl dicarbonate were dissolved in a mixture of 250 mL of 2 N sodium hydroxide and 250 mL of trifluorotoluene, and the resulting mixture was heated to 45° C. The reaction mixture was allowed to agitate for 3 days. An additional 30 g (0.14 mole) of ditert.butyl dicarbonate was added stepwise. The organic layer was then separated, and the aqueous phase was extracted twice with 100-mL portions of dichloromethane. The combined extracts were evaporated, and the residue was taken up in 200 mL of hexane. The precipitate was filtered off and washed with 50 mL of hexane.

This gave 18.6 g (82% of the theoretical) of 2,5-tert.butylcarbonylaminobromobenzene with a melting point at 130° C.

B. Synthesis of 2,5-Diamino-1-phenylbenzene derivatives of Formula (I)

3.3 g (0.01 mole) of 2,5-tert.butyloxycarbonylaminobromobenzene from step A and 0.013 mole of the desired boric acid derivative were dissolved in 70 mL of 1,2-dimethoxyethane under argon. Then, 0.5 g of tetrakis(triphenylphosphine)palladium (0.0005 mole) and 13 mL of 2 N potassium carbonate solution were added, the reaction mixture was poured into 100 mL of ethyl acetate. The organic phase was extracted with dilute sodium hydroxide solution and then dried over magnesium sulfate. The solvent was distilled off from a rotary evaporator and the residue was purified [by column chromatography] on silica gel using petroleum ether/ethyl acetate (9:1) [for elution]. The resulting product was dissolved in 40 mL of ethanol and the solution was heated to 50° C.

To prepare the hydrochloride, 15 mL of a 2.9 molar ethanolic hydrochloric acid solution was added dropwise. The precipitate was filtered off, washed twice with 10-mL portions of ethanol and dried.

a) 2,5-Diamino-1-phenylbenzene Dihydrochloride

Boric acid used: phenylboric acid
Yield: 1.8 g (72% of the theoretical)
Melting point: 250° C. (colorless crystals).

| CHN analysis ($C_{12}H_{14}N_2Cl_2$) | | |
|---|---|---|
| % C | % H | % N |
| Calcd. 56.06 | 5.49 | 10.89 |
| Found 55.95 | 5.46 | 10.58 | b) 2,5-Diamino-1-(3-nitrophenyl)benzene Dihydrochloride
Boric acid used: 3-nitrophenylboric acid
Yield: 1.9 g (65% of the theoretical)

Melting point: 245° C. (colorless crystals).

CHN analysis ($C_{12}H_{13}N_3O_2Cl_2$)

|  | % C | % H | % N |
|---|---|---|---|
| Calcd. | 47.70 | 4.34 | 13.91 |
| Found | 47.89 | 4.28 | 13.78 | c) 2,5-Diamino-(1-3-methoxyphenyl)benzene Dihydrochloride
Boric acid used: 3-methoxyphenylboric acid
Yield: 2.01 g (72% of the theoretical)
Melting point: 255° C. (colorless crystals).

CHN analysis ($C_{13}H_{16}N_2OCl_2$)

|  | % C | % H | % N |
|---|---|---|---|
| Calcd. | 54.37 | 5.62 | 9.75 |
| Found | 54.25 | 5.59 | 9.60 | d) 2,5-Diamino-1-(4-methoxyphenyl)benzene Dihydrochloride
Boric acid used: 4-methoxyphenylboric acid
Yield: 2.2 g (77% of the theoretical)
Melting point: 250° C. (colorless crystals).

CHN analysis ($C_{13}H_{16}N_2OCl_2$)

|  | % C | % H | % N |
|---|---|---|---|
| Calcd. | 54.37 | 5.62 | 9.75 |
| Found | 54.51 | 5.32 | 9.64 | e) 2,5-Diamino-1-(3-aminophenyl)benzene Dihydrochloride
Boric acid used: 3-aminophenylboric acid
Yield: 0.6 g (20% of the theoretical)
Melting point: 260° C. (colorless crystals).

CHN analysis ($C_{12}H_{16}N_3Cl_3$)

|  | % C | % H | % N |
|---|---|---|---|
| Calcd. | 46.7 | 5.23 | 13.61 |
| Found | 46.47 | 5.48 | 11.94 |

C. Synthesis of N,N'-bis(tert.Butoxycarbonyl)-2,5-diamino-1-phenylboric Acid

N,N'-bis(tert.Butoxycarbonyl)-2,5-diamino-1-phenylboric acid was prepared by reaction of N,N'-bis(tert.butoxycarbonyl)-2,5-diamino-1-bromobenzene with tert.butyllithium and trimethyl borate. The experimental procedure for this method of preparation has been described by J. M. Tour and J. J. S. Lamba in J. Am. Chem. Soc. 116, 11723 (1994).

D. Synthesis of 2,5-Diamino-1-phenylbenzenes 0.035 g (0.0001 mole) of 2,5-tert.butyloxycarbonylamino-1-phenylboric acid from step C and 0.00015 mole of the desired bromo derivative were dissolved in 10 mL of 1,2-dimethoxyethane under argon. Then, 0.005 g of tetrakis(phenylphoshphine)-palladium (0.000005 mole) and 0.13 mL of 2 N potassium carbonate solution were added, and the reaction mixture was heated to 80° C. At the end of the reaction, the reaction mixture was poured into 10 mL of ethyl acetate, the organic phase was extracted with dilute sodium hydroxide solution and then dried over magnesium sulfate. The solvent was distilled off from a rotary evaporator, and the residue was purified [by column chromatography] over silica gel using petroleum ether/ethyl acetate (9:1) [as the eluent]. The resulting product was dissolved in 4-mL of ethanol, and the solution was heated to 50° C.

To prepare the hydrochloride, 1.5 mL of a 2.9 molar ethanolic hydrochloric acid solution was added dropwise. The precipitate was filtered off, washed twice with 1-mL portions of ethanol and then dried.

a) 2,5-Diamino-1-(4-nirophenyl)benzene Dihydrochloride
Bromo derivative used: 1-bromo-4-nitrobenzene
Yield: 0.025 g (80% of the theoretical)
Mass spectrum MH$^+$: 230 (100)

b) 2,5-Diamino-1-(4-chlorophenyl)benzene Dihydrochloride
Bromo derivative used: 1-bromo-4-chlorobenzene
Yield: 0.025 g (86% of the theoretical)
Mass spectrum MH$^+$: 219 (100)

c) 2,5-Diamino-1-(4-trifluoromethylphenyl)benzene Dihydrochloride
Bromo derivative used: 1-bromo-4-trifluoromethylbenzene
Yield: 0.025 g (78% of the theoretical)
Mass spectrum MH$^+$: 253 (100)

d) 2,5-Diamino-1-(4-cyanophenyl)benzene Dihydrochloride
Bromo derivative used: 1-bromo-4-cyanobenzene
Yield: 0.025 g (90% of the theoretical)
Mass spectrum MH$^+$: 210 (100)

e) 2,5-Diamino-1-(4-methylphenyl)benzene Dihydrochloride
Bromo derivative used: 1-bromo-4-methylbenzene
Yield: 0.025 g (92% of the theoretical)
Mass spectrum MH$^+$: 199 (100)

f) 2,5-Diamino-1-(4-hydroxyphenyl)benzene Dihydrochloride
Bromo derivative used: 4-bromophenol
Yield: 0.025 g (92% of the theoretical)
Mass spectrum MH$^+$: 201 (100)

g) 2,5-Diamino-1-(4-aminophenyl)benzene Dihydrochloride
Bromo derivative used: 4-bromoaniline
Yield: 0.025 g (90% of the theoretical)
Mass spectrum MH$^+$: 200 (100)

h) 2,5-Diamino-1-(4-ethylcarboxyphenyl)benzene Dihydrochloride
Bromo derivative used: ethyl 1-bromobenzoate
Yield: 0.025 g (75% of the theoretical)
Mass spectrum MH$^+$: 257 (100)

i) 2,5-Diamino-1-(3-nitro-4-trifluoromethyl)benzene Dihydrochloride
Bromo derivative used: 1-bromo-3-nitro-4-trifluoromethylbenzene
Yield: 0.025 g (65% of the theoretical)
Mass spectrum MH$^+$: 298 (100)

j) 2,5-Diamino-1-phenoxyphenyl)benzene Dihydrochloride
Bromo derivative used: 1-bromo-4-phenoxybenzene
Yield: 0.025 g (70% of the theoretical)
Mass spectrum MH$^+$: 277 (100)

k) 2,5-Diamino-1-(2-methoxy-5-cyanophenyl)benzene Dihydrochloride

Bromo derivative used: 1-bromo-2-methoxy-5-cyanobenzene
Yield: 0.025 g (80% of the theoretical)
Mass spectrum MH⁺: 240 (100)

l) 2,5-Diamino-1-(3-nitro-4-methylphenyl)benzene Dihydrochloride
Bromo derivative used: 1-bromo-3-nitro-4-methylbenzene
Yield: 0.025 g (78% of the theoretical)
Mass spectrum MH⁺: 244 (100)

m) 2,5-Diamino-1-(2-nitro-4-methylphenyl)benzene Dihydrochloride
Bromo derivative used: 1-bromo-2-nitro-4-methylbenzene
Yield: 0.025 g (78% of the theoretical)
Mass spectrum MH⁺: 244 (100)

n) 2,5-Diamino-1-(3-trifluoromethyl-4-nitrophenyl)benzene Dihydrochloride
Bromo derivative used: 1-bromo-3-trifluoromethyl-4-nitrobenzene
Yield: 0.025 g (67% of the theoretical)
Mass spectrum MH⁺: 298 (100)

o) 2,5-Diamino-1-(2,4-dimethoxyphenyl)benzene Dihydrochloride
Bromo derivative used: 1-bromo-2,4-dimethoxybenzene
Yield: 0.025 g (78% of the theoretical)
Mass spectrum MH⁺: 245 (100)

p) 2,5-Diamino-1-(2-methyl-3-nitrophenyl)benzene Dihydrochloride
Bromo derivative used: 1-bromo-2-methyl-3-nitrobenzene
Yield: 0.025 g (78% of the theoretical)
Mass spectrum MH⁺: 244 (100)

q) 2,5-Diamino-1-(3,4-dimethoxyphenyl)benzene Dihydrochloride
Bromo derivative used: 1-bromo-3,4-dimethoxybenzene
Yield: 0.025 g (78% of the theoretical)
Mass spectrum MH⁺: 245 (100)

r) 2,5-Diamino-1-(2,5-dimethoxyphenyl)benzene Dihydrochloride
Bromo derivative used: 1-bromo-2,5-dimethoxybenzene
Yield: 0.025 g (78% of the theoretical)
Mass spectrum MH⁺: 245 (100)

s) 2,5-Diamino-1-(2-methyl-4-nitrophenyl)benzene Dihydrochloride
Bromo derivative used: 1-bromo-2-methyl-4-nitrobenzene
Yield: 0.025 g (78% of the theoretical)
Mass spectrum MH⁺: 244 (100)

t) 2,5-Diamino-1-(2-methyl-5-nitrophenyl)benzene Dihydrochloride
Bromo derivative used: 1-bromo-2-methyl-5-nitrobenzene
Yield: 0.025 g (78% of the theoretical)
Mass spectrum MH⁺: 244 (100)

u) 2,5-Diamino-1-[4-(1-oxypentyl)phenyl]benzene Dihydrochloride
Bromo derivative used: 1-(4-bromophenyl)-1-pentan-1-one
Yield: 0.025 g (78% of the theoretical)
Mass spectrum MH⁺: 269 (100)

v) 2,5-Diamino-3-fbiphenyl)benzene Dihydrochloride
Bromo derivative used: 3-bromophenyl
Yield: 0.025 g (76% of the theoretical)
Mass spectrum MH⁺: 261 (100)

w) 2,5-Diamino-1-(2,5-dimethylphenyl)benzene
Bromo derivative used: 1-bromo-2,5-dimethylbenzene
Yield: 0.025 g (89% of the theoretical)
Mass spectrum MH⁺: 213 (100)

x) 2,5-Diamino-1-(2-chloro-5-nitrophenyl)benzene Dihydrochlodde
Bromo derivative used: 1-bromo-2-chloro-5-nitrobenzene
Yield: 0.025 g (73% of the theoretical)
Mass spectrum MH⁺: 265 (100)

y) 2,5-Diamino-1-(2-methyl-4-hydroxyphenyl)benzene Dihydrochloride
Bromo derivative used: 1-bromo-2-methyl-4-hydroxybenzene
Yield: 0.025 g (86% of the theoretical)
Mass spectrum MH⁺: 215 (100)

z) 2,5-Diamino-1-(indan-1-on-5-yl)benzene Dihydrochloride
Bromo derivative used: 5-bromo-1-1-indanone
Yield: 0.025 g (80% of the theoretical)
Mass spectrum MH⁺: 239 (100)

a') 2,5-Diamino-1-(2-methylmethoxyphenyl)benzene Dihydrochloride
Bromo derivative used: 1-bromo-2-methyl-4-methoxybenzene
Yield: 0.025 g (83% of the theoretical)
Mass spectrum MH⁺: 229 (100)

b') 2,5-Diamino-1-(2,4-dichlorophenyl)benzene Dihydrochloride
Bromo derivative used: 1-bromo-2,4-dichlorobenzene
Yield: 0.025 g (77% of the theoretical)
Mass spectrum MH⁺: 253 (100)

c') 2,5-Diamino-1-(2,3-methylenedioxyphenyl]benzene Dihydrochloride
Bromo derivative used: 1-bromo-2,3-methylenedioxybenzene
Yield: 0.025 g (83% of the theoretical)
Mass spectrum MH⁺: 229 (100)

d') 2.5-Diamino-1-(3-trifluoromethyl-4-chlorophenyl)benzene Dihydrochloride
Bromo derivative used: 1-bromo-3-trifluoromethyl-4-chlorobenzene
Yield: 0.025 g (70% of the theoretical)
Mass spectrum MH⁺: 287 (100)

e') 2,5-Diamino-1-(3,5-dimethylphenyl)benzene Dihydrochloride
Bromo derivative used: 1-bromo-3,5-dimethylbenzene
Yield: 0.025 g (88% of the theoretical)
Mass spectrum MH⁺: 213 (100)

f') 2,5-Diamino-1-(3,4-dimethylphenyl)benzene Dihydrochloride
Bromo derivative used: 1-bromo-3,4-dimethylbenzene
Yield: 0.025 g (88% of the theoretical)
Mass spectrum MH⁺: 212 (100)

g') 2,5-Diamino-1-(3-chlorophenyl)benzene Dihydrochloride
Bromo derivative used: 1-bromo-3-chlorobenzene
Yield: 0.025 g (86% of the theoretical)
Mass spectrum MH⁺: 219 (100)

h') 2,5-Diamino-1-(3-trifluoromethylphenyl)benzene Dihydrochloride
Bromo derivative used: 1-bromo-3-trifluoromethylbenzene
Yield: 0.025 g (77% of the theoretical)
Mass spectrum MH+(+CH₃CN): 294 (100)

i') 2,5-Diamino-1-(2-methoxyphenyl)benzene Dihydrochloride
Bromo derivative used: 1-bromo-2-methoxybenzene
Yield: 0.025 g (87% of the theoretical)
Mass spectrum MH⁺: 215 (100)

j') 2,5-Diamino-1-(4-ethoxyphenyl)benzene Dihydrochloride
Bromo derivative used: 1-bromo-4-ethoxybenzene
Yield: 0.025 g (83% of the theoretical)
Mass spectrum MH⁺: 229 (100)

k') 2,5-Diamino-1-(4-fluorophenyl)benzene Dihydrochloride

Bromo derivative used: 1-bromo-4-fluorobenzene
Yield: 0.025 g (91% of the theoretical)
Mass spectrum MH$^+$: 203 (100)

l') 2,5-Diamino-1-(carboxamidophenyl)benzene Dihydrochloride
Bromo derivative used: 4-bromobenzamide
Yield: 0.025 g (83% of the theoretical)
Mass spectrum MH$^+$: 228 (100)

m') 2,5-Diamino-1-(2-nitro-4-methoxyphenyl)benzene Dihydrochloride
Bromo derivative used: 1-bromo-2-nitro-4-methoxybenzene
Yield: 0.025 g (75% of the theoretical)
Mass spectrum MH$^+$: 260 (100)

n') 2,5-Diamino-1-(1-acetyl-2,3-dihydroindol-5-yl)benzene Dihydrochloride
Bromo derivative used: 1-acetyl-2,3-dihydro-5-bromoindol
Yield: 0.025 g (73% of the theoretical)
Mass spectrum MH$^+$: 268 (100)

o') 2,5-Diamino-1-(2,4-dimethoxy-3-carboxamidophenyl)benzene Dihydrochloride
Bromo derivative used: 3-bromo-2,6-dimethoxybenzamide
Yield: 0.025 g (69% of the theoretical)
Mass spectrum MH$^+$: 288 (100)

p') 2,5-Diamino-1-(2-chloro-4-nitrophenyl)benzene Dihydrochloride
Bromo derivative used: 1-bromo-2-chloro-4-nitrobenzene
Yield: 0.025 g (74% of the theoretical)
Mass spectrum MH$^+$: 264 (100)

q') 2,5-Diamino-1-(2,5-difluoro-4-nitrophenyl)benzene Dihydrochloride
Bromo derivative used: 1-bromo-2,5-difluoro-4-nitrobenzene
Yield: 0.025 g (74% of the theoretical)
Mass spectrum MH$^+$: 266 (100)

r') 2,5-Diamino-1-(2-chloro-4-N-acetylaminophenyl)benzene Dihydrochloride
Bromo derivative used: 4-bromo-2-chloroacetanilide
Yield: 0.025 g (72% of the theoretical)
Mass spectrum MH$^+$: 276 (100)

s') 2,5-Diamino-1-(indol-5-yl)benzene Dihydrochloride
Bromo derivative used: 1-bromoindol
Yield: 0.025 g (84% of the theoretical)
Mass spectrum MH$^+$: 224 (100)

t') 2,5-Diamino-1-(3,5-dichlorophenyl)benzene Dihydrochloride
Bromo derivative used: 1-bromo-3,5-dichloropbenzene
Yield: 0.025 g (77% of the theoretical)
Mass spectrum MH$^+$: 253 (100)

u') 2,5-Diamino-1-(2,4,5-trimethylphenyl)benzene Dihydrochloride
Bromo derivative used: 1-bromo-2,4,5-trimethylbenzene
Yield: 0.025 g (84% of the theoretical)
Mass spectrum MH$^+$: 227 (100)

v') 2,5-Diamino-1-(2,4-dimethylphenyl)benzene Dihydrochloride
Bromo derivative used: 1-bromo-2,4-dimethylbenzene
Yield: 0.025 g (88% of the theoretical)
Mass spectrum MH$^+$: 213 (100)

w') 2,5-Diamino-1-(2,3-dimethylphenyl)benzene Dihydrochloride
Bromo derivative used: 1-bromo-2,3-dimethylbenzene
Yield: 0.025 g (88% of the theoretical)
Mass spectrum MH$^+$: 213 (100)

x') 2,5-Diamino-1-(3-fluorophenyl)benzene Dihydrochloride
Bromo derivative used: 1-bromo-3-fluorobenzene
Yield: 0.025 g (91% of the theoretical)
Mass spectrum MH$^+$: 203 (100)

y') 2,5-Diamino-1-(3-cyanophenyl)benzene Dihydrochloride
Bromo derivative used: 1-bromo-3-cyanobenzene
Yield: 0.025 g (89% of the theoretical)
Mass spectrum MH$^+$: 210 (100)

z') 2,5-Diamino-1-(3-methylphenyl)benzene Dihydrochloride
Bromo derivative used: 1-bromo-3-methylbenzene
Yield: 0.025 g (92% of the theoretical)
Mass spectrum MH$^+$: 199 (100)

a") 2,5-Diamino-1-(3-hydroxyphenyl)benzene Dihydrochloride
Bromo derivative used: 1-bromo-3-hydroxybenzene
Yield: 0.025 g (92% of the theoretical)
Mass spectrum MH$^+$: 201 (100)

b") 2,5-Diamino-1-(3-aminomethylphenyl)benzene Dihydrochloride
Bromo derivative used: 1-bromo-3-aminomethylbenzene
Yield: 0.025 g (77% of the theoretical)
Mass spectrum MH$^+$: 214 (100)

c") 2,5-Diamino-1-(3-carboxythylphenyl)benzene Dihydrochloride
Bromo derivative used: ethyl 3-bromobenzoate
Yield: 0.025 g (76% of the theoretical)
Mass spectrum MH$^+$: 257 (100)

d") 2,5-Diamino-1-(2-nitrophenyl)benzene Dihydrochloride
Bromo derivative used: 1-bromo-2-nitrobenzene
Yield: 0.025 g (83% of the theoretical)
Mass spectrum MH$^+$: 230 (100)

e') 2,5-Diamino-1-(2-fluorophenyl)benzene Dihydrochloride
Bromo derivative used: 1-bromo-2-fluorobenzene
Yield: 0.025 g (91% of the theoretical)
Mass spectrum MH$^+$: 203 (100)

f") 2,5-Diamino-1-(2-chlorophenyl)benzene Dihydrochloride
Bromo derivative used: 1-bromo-2-chlorobenzene
Yield: 0.025 g (86% of the theoretical)
Mass spectrum MH$^+$: 219 (100)

g") 2,5-Diamino-1-(2-trifluoromethylphenyl)benzene Dihydrochloride
Bromo derivative used: 1-bromo-2-trifluoromethylbenzene
Yield: 0.025 g (77% of the theoretical)
Mass spectrum MH$^+$: 253 (100)

h") 2,5-Diamino-1-(2-methylphenyl)benzene Dihydrochloride
Bromo derivative used: 1-bromo-2-methylbenzene
Yield: 0.025 g (92% of the theoretical)
Mass spectrum MH$^+$: 199 (100)

i") 2,5-Diamino-1-(2-cyanomethylphenyl)benzene Dihydrochloride
Bromo derivative used: 1-bromo-2-cyanomethylbenzene
Yield: 0.025 g (84% of the theoretical)
Mass spectrum MH$^+$: 224 (100)

j") 2,5-Diamino-1-(4-ethylphenyl)benzene Dihydrochloride
Bromo derivative used: 1-bromo-4-ethyl)benzene
Yield: 0.025 g (88% of the theoretical)
Mass spectrum MH$^+$: 213 (100)

k") 2,5-Diamino-1-(4-propylphenyl)benzene Dihydrochloride
Bromo derivative used: 1-bromo-4-propyl)benzene
Yield: 0.025 g (84% of the theoretical)
Mass spectrum MH$^+$: 227 (100)

l") 2,5-Diamino-1-(4 isopropylphenyl)benzene Dihydrochloride

Bromo derivative used: 1-bromo-4-isopropylbenzene
Yield: 0.025 g (84% of the theoretical)
Mass spectrum MH⁺: 227 (100)

m") 2,5-Diamino-1-(4-butylphenyl)benzene Dihydrochloride
Bromo derivative used: 1-bromo-4-butylbenzene
Yield: 0.025 g (80% of the theoretical)
Mass spectrum MH⁺: 241 (100)

n") 2,5-Diamino-1-(4-tert.butylphenyl)benzene Dihydrochloride
Bromo derivative used: 1-bromo-4-tert.butylbenzene
Yield: 0.025 g (80% of the theoretical)
Mass spectrum MH⁺: 241 (100)

o") 2,5-Diamino-1-(4-pentylphenyl)benzene Dihydrochloride
Bromo derivative used: 1-bromo-4-pentylbenzene
Yield: 0.025 g (76% of the theoretical)
Mass spectrum MH⁺: 255 (100)

p") 2,5-Diamino-1-(4-acetylphenyl)benzene Dihydrochloride
Bromo derivative used: 1-bromo-4-acetylbenzene
Yield: 0.025 g (84% of the theoretical)
Mass spectrum MH⁺: 227 (100)

q") 2,5-Diamino-1-(4-thiomethoxyphenyl)benzene Dihydrochloride
Bromo derivative used: 1-bromo-4-thiomethoxybenzene
Yield: 0.025 g (91% of the theoretical)
Mass spectrum MH⁺: 203 (100)

r") 2,5-Diamino-1-(2-ethylphenyl)benzene Dihydrochloride
Bromo derivative used: 1-bromo-2-ethylbenzene
Yield: 0.025 g (88% of the theoretical)
Mass spectrum MH⁺: 213 (100)

s") 2,5-Diamino-1-(2-fluoro-4-methylphenyl)benzene Dihydrochloride
Bromo derivative used: 1-bromo-2-fluoro-4-methylbenzene
Yield: 0.025 g (86% of the theoretical)
Mass spectrum MH⁺: 217 (100)

t") 2,5-Diamino-1-(2-methyl-5-fluorophenyl)benzene Dihydrochloride
Bromo derivative used: 1-bromo-2-methyl-5-fluorobenzene
Yield: 0.025 g (86% of the theoretical)
Mass spectrum MH⁺: 217 (100)

u") 2,5-Diamino-1-(2-thiomethoxyphenyl)benzene Dihydrochloride
Bromo derivative used: 1-bromo-2-thiomethoxybenzene
Yield: 0.025 g (82% of the theoretical)
Mass spectrum MH⁺: 231 (100)

v") 2,5-Diamino-1-(2,3-dichlorophenyl)benzene Dihydrochloride
Bromo derivative used: 1-bromo-2,3-dichlorobenzene
Yield: 0.025 g (77% of the theoretical)
Mass spectrum MH⁺: 253 (100)

w") 2,5-Diamino-4-(4'-hydroxybiphenyl)benzene Dihydrochloride
Bromo derivative used: 4-bromo-4'-hydroxybiphenyl
Yield: 0.025 g (72% of the theoretical)
Mass spectrum MH⁺: 277 (100)

x") 2,5-Diamino-1-(3-ethoxyphenyl)benzene Dihydrochloride
Bromo derivative used: 1-bromo-3-ethoxybenzene
Yield: 0.025 g (77% of the theoretical)
Mass spectrum MH⁺: 229 (100)

y") 2,5-Diamino-1-([42-pyrrolidin-1-ylethoxy)phenyl]benzene Dihydrochloride
Bromo derivative used: 1-bromo-4-(2-pyrrolidin-1-ylethoxy)benzene
Yield: 0.025 g (61% of the theoretical)
Mass spectrum MH⁺: 298 (100)

z") 2,5-Diamino-1-([4-(1-hydroxyethyl)phenyl]benzene Dihydrochloride
Bromo derivative used: 1-bromo-4-(1-hydroxyethyl)benzene
Yield: 0.025 g (83% of the theoretical)
Mass spectrum MH⁺: 229 (100)

a'") 2,5-Diamino-1-(2,4-trifluoromethylphenyl)benzene Dihydrochloride
Bromo derivative used: 1-bromo-2,4-trifluoromethylbenzene
Yield: 0.025 g (64% of the theoretical)
Mass spectrum MH⁺: 321 (100)

b'") 2,5-Diamino-1-(2-fluoro-5-acetylphenyl)benzene Dihydrochloride
Bromo derivative used: 1-bromo-2-fluoro-5-acetylbenzene
Yield: 0.025 g (79% of the theoretical)
Mass spectrum MH⁺: 245 (100)

c'") 2,5-Diamino-1-(3-fluoro-4-methoxyphenyl)benzene Dihydrochloride
Bromo derivative used: 1-bromo-3-fluoro-4-methoxybenzene
Yield: 0.025 g (82% of the theoretical)
Mass spectrum MH⁺: 233 (100)

d'") 2,5-Diamino-1-(3-acetyl-4hydroxyphenyl)benzene Dihydrochloride
Bromo derivative used: 1-bromo-3-acetyl-4-hydroxybenzene
Yield: 0.025 g (79% of the theoretical)
Mass spectrum MH⁺: 243 (100)

e'") 2,5-Diamino-1-[4-(2-hydroxyethyl)phenyl]benzene Dihydrochloride
Bromo derivative used: 1-bromo-4-(2-hydroxyethyl)benzene
Yield: 0.025 g (79% of the theoretical)
Mass spectrum MH⁺: 245 (100)

f'") 2,5-Diamino-1-[4-(propyl-1-one)phenyl]benzene Dihydrochloride
Bromo derivative used: 1-bromo-4-(propyl-1-one)benzene
Yield: 0.025 g (80% of the theoretical)
Mass spectrum MH⁺: 241 (100)

g'") 2,5-Diamino-1-(4-N,N-diisopropylaminomethylphenyl)benzene Dihydrochloride
Bromo derivative used: 1-bromo-4-N,N-diisopropylaminomethylbenzene
Yield: 0.025 g (61% of the theoretical)
Mass spectrum MH⁺: 298 (100)

h'") 2,5-Diamino-1-(3-acetyiphenyl)benzene Dihydrochloride
Bromo derivative used: 1-bromo-3-acetylbenzene
Yield: 0.025 g (84% of the theoretical)
Mass spectrum MH⁺: 227 (100)

i'") 2,5-Diamino-1-[2-(2-hydroxyethyl)phenyl]benzene Dihydrochloride
Bromo derivative used: 1-bromo-2-(2-hydroxyethyl)benzene
Yield: 0.025 g (83% of the theoretical)
Mass spectrum MH⁺: 229 (100)

j'") 2,5-Diamino-1-(4-methoxyphenyl)benzene Dihydrochloride
Bromo derivative used: 4-bromoanisole
Yield: 0.025 g (87% of the theoretical)
Mass spectrum MH⁺: 215 (100)

Example 2

Synthesis of 2,5-Diamino-4-methoxy-1-phenylbenzene. 2 HCl

A) Synthesis of 2-Amino-4-methoxy-5-nitro-1-phenylbenzene
2.02 g (0.01 mole) of 4-chloro-5-nitro-2-aminoanisole and 0.013 mole of phenylboric acid were dissolved in 70 mL of 1,2-dimethoxyethane under argon. Then, 0.5 g (0.0005 mole) of tetrakis(triphenylphosphine)palladium and 13 mL of 2 N potassium carbonate solution were added, and the reaction mixture was heated to 80° C. At the end of the reaction, the reaction mixture was poured into 100 mL of ethyl acetate. The organic phase was extracted with dilute sodium hydroxide solution and then dried over magnesium sulfate. The solvent was distilled off from a rotary evaporator, and the residue was purified [by column chromatography] on silica gel using hexane/ethyl acetate (8:1) [as the eluent].
Yield: 1.54 g (63% of the theoretical)
M.p.: 105–109° C. (yellow crystals)
B. Synthesis of 2,5-Diamino-4-methoxy-1-phenylbenzene.2 HCl 0.5 g (2-mmoles) of 2-amino-4-methoxy-5-nitro-1-phenylbenzene (A) was dissolved in 30 mL of ethanol and after addition of 100 mg of a palladium-on-active carbon catalyst (10%) hydrogenated at 25° C. After the theoretical amount of hydrogen had been absorbed, the catalyst was filtered off and excess dilute hydrochloric acid was added to the filtrate. The solution was evaporated in a rotary evaporator, after which the precipitated hydrochloride was filtered off and dried.
Yield: 0.53 g (93% of the theoretical)
M.p.: 257–260° C. (colorless crystals)

| CHN analysis ($C_{13}H_{16}N_2OCl_2$) | | | |
|---|---|---|---|
| | % C | % H | % N |
| Calcd. | 54.37 | 5.62 | 9.75 |
| Found | 54.09 | 5.42 | 9.62 |

Example 3

Synthesis of 2,5-Diamino-4-methyl-1-phenylbenzene. 2 HCl

A. Synthesis of 2-Amino-4-methyl-5-nitro-1-phenylbenzene 1.87 g (0.01 mole) of 5-chloro-2-methyl-4-nitroaniline and 0.013 mole of phenylboric acid were dissolved in 70 mL of 1,2-dimethoxyethane under argon. Then, 0.5 g (0.0005 mole) of tetrakis(triphenylphosphine)palladium and 13 mL of 2 N potassium carbonate solution were added, and the reaction mixture was heated to 80° C. At the end of the reaction, the reaction mixture was poured into 100 mL of ethyl acetate. The organic phase was extracted with dilute sodium hydroxide solution and then dried over magnesium sulfate. The solvent was distilled off from a rotary evaporator, and the residue was purified [by column chromatography] on silica gel using hexane/ethyl acetate (8:1) [as the eluent].
Yield: 2.05 g (90% of the theoretical)
NMR
(500 MHz, $CDCl_3$) 7.82 (s. 1H); 7.4–7.3 (m, 3H); 7.2 (d, 2H); 6.45 (s, 1H); 6.3 (s, 2H); 2.13 (s, 3H).
B. Synthesis of 2.5-Diamino-4-methyl-1-phenylbenzene.2 HCl 0.5 g (2-mmoles) of 2-amino-4-methyl-5-nitro-1-phenylbenzene (A) was dissolved in 30 mL of ethanol and after addition of 100 mg of a palladium-on-active carbon catalyst (10%) hydrogenated at 25° C. After the theoretical amount of hydrogen had been absorbed, the catalyst was filtered off and excess dilute hydrochloric acid was added to the filtrate. The solution was evaporated in a rotary evaporator, after which the precipitated hydrochloride was filtered off and dried.
Yield: 0.50 g (93% of the theoretical)
M.p.: 263–265° C. (colorless crystals)

| CHN analysis ($C_{13}H_{16}N_2Cl_2$) | | | |
|---|---|---|---|
| | % C | % H | % N |
| Calcd. | 54.37 | 5.62 | 9.75 |
| Found | 54.09 | 5.42 | 9.62 |

Example 4

Synthesis of 2-Alkylamino-5-amino-1-phenylbenzenes of General Formula (I).

(General Method of Synthesis)
A) Synthesis of 2-Fluoro-5-nitro-1-phenylbenzene
1.75 g (0.01 mole) of 3-chloro-4-fluoronitrobenzene and 0.013 mole of phenylboric acid were dissolved in 70 mL of 1,2-dimethoxyethane under argon. Then, 0.5 g (0.0005 mole) of tetrakis(triphenylphosphine)palladium and 13 mL of 2N potassium carbonate solution were added, and the reaction mixture was heated to 80° C. At the end of the reaction, the reaction mixture was poured into 100 mL of ethyl acetate. The organic phase was extracted with dilute sodium hydroxide solution and then dried over magnesium sulfate. The solvent was distilled off from a rotary evaporator, and the residue was purified [by column chromatography] on silica gel using hexane/toluene (10:1) [as the eluent].
Yield: 2.05 g (94% of the theoretical)
NMR
(250 MHz, $CDCl_3$) 8.39 (dd, 1H); 8.25–8.21 (m, 1H); 7.57 (d, 2H); 7.5–7.46 (m, 3H); 7.31 (t, 1H).
B) Synthesis of 2-Alkylamino-5-nitro-1-phenylbenzene of Formula (I).

(General Method of Synthesis)
2.2 g (0.01 mole) of 2-fluoro-5-nitro-1-phenylbenzene (A) was dissolved in 25 mL of ethanol. Then, 0.05 mole of the desired amine was added at reflux. At the end of the reaction, the reaction mixture was poured into water and the aqueous phase was extracted with ethyl acetate. The organic phase was dried over magnesium sulfate. The solvent was distilled off from a rotary evaporator, and the residue was purified [by column chromatography] over silica gel using hexane/ethyl acetate (20:1) [as the eluent].
a) 2-Dimethylamino-5-nitro-1-phenylbenzene
Amine used: dimethylamine
Yield: 2.1 g (87% of the theoretical)
M.p.: 70–73° C. (yellow crystals)
b) 2-Di-(2-hydroxyethyl)amino-5-nitro-1-phenylibenzene
Amine used: diethanolamine
Yield: 0.5 g (18% of the theoretical)
Orange-colored oil
NMR
(500 MHz, $CDCl_3$): 8.13 (dd, 1H); 8.06 (d, 1H); 7.47–7.26 (m, 6H); 3.6–3.58 (m, 4H); 3.3–3.27 (m, 4H).
c) 2-Pyrrolidino-5-nitro-1-phenylbenzene
Amine used: pyrrolidine
Yield: 2.5 g (93% of the theoretical)
M.p.: 109–113° C. (yellow crystals)

d) 2-(2-Hydroxyethyl)amino-5-nitro-1-phenylbenzene
Amine used: ethanolamine
Yield: 2.5 g (96% of the theoretical)
Orange-colored oil
NMR
(500 MHz, CDCl$_3$): 8.14 (dd, 1H); 8.00 (s, 1H); 7.5–7.4 (m, 5H); 6.67 (d, 1H); 5.1 (s, 1H); 3.84–3.82 (dd, 2H); 3.4–3.37 (dd, 2H).
e) 2-(2-Methoxyethyl)amino-5-nitro-1-phenylbenzene
Amine used: 2-methoxyethylamine
Yield: 2.6 g (96% of the theoretical)
M.p.: 93–95° C. (yellow crystals)
f) 2-(2,3-Dihydroxypropyl)amino-5-nitro-1-phenylbenzene
Amine used: 2,3-dihydroxypropylamine
Yield: 2.6 g (90% of the theoretical)
M.p.: 127–131° C. (orange crystals)

C. Synthesis of 2-Alkylamino-1-phenylbenzenes of General Formula (I).

(General Method of Synthesis)

2-mmoles of 2-alkylamino-5-nitro-1-phenylbenzene (B) was dissolved in 30 mL of ethanol and after addition of 100 mg of a palladium-on-active carbon catalyst (10%) hydrogenated at 25° C. After the theoretical amount of hydrogen had been absorbed, the catalyst was filtered off and excess dilute hydrochloric acid was added to the filtrate. The solution was evaporated in a rotary evaporator, after which the precipitated hydrochloride was filtered off and dried.

a) 2-Di-(2-dimethylamino-5-amino-1-phenylbenzene Dihydrochloride
Yield: 0.33 g (77% of the theoretical)
M.p.: 220–225° C. (colorless crystals)

CHN analysis ($C_{14}H_{18}N_2Cl_2$)

|  | % C | % H | % N |
|---|---|---|---|
| Calcd. | 58.96 | 6.36 | 9.82 |
| Found | 58.75 | 6.43 | 9.61 | b) 2-Di-(2-hydroxyethyl)amino-5-amino-1-phenylbenzene Dihydrochloride
Yield: 0.6 g (80% of the theoretical)
M.p.: 222–225° C. (colorless crystals)

CHN analysis ($C_{16}H_{22}N_2O_2Cl_2$)

|  | % C | % H | % N |
|---|---|---|---|
| Calcd. | 55.66 | 6.42 | 8.11 |
| Found | 55.21 | 6.21 | 7.96 | c) 2-Pyrrolidino-5-amino-1-phenylbenzene Dihydrochloride
Yield: 0.41 g (87% of the theoretical)
M.p.: 256–261° C. (colorless crystals)

CHN analysis ($C_{16}H_{20}N_2Cl_2$)

|  | % C | % H | % N |
|---|---|---|---|
| Calcd. | 61.74 | 6.48 | 9.00 |
| Found | 61.00 | 6.81 | 8.65 | d) 2-(2-Hydroxyethyl)amino-5-amino-1-phenylbenzene Dihydrochloride
Yield: 0.47 g (92% of the theoretical)
M.p.: 210–213° C. (colorless crystals)

CHN analysis ($C_{14}H_{18}N_2OCl_2$)

|  | % C | % H | % N |
|---|---|---|---|
| Calcd. | 55.83 | 6.02 | 9.30 |
| Found | 55.71 | 6.25 | 9.43 | e) 2-(2-Methoxyethyl)amino-5-amino-1-phenylbenzene Dihydrochloride
Yield: 0.47 g (94% of the theoretical)
M.p.: 74° C. (decomposition) (colorless crystals)

CHN analysis ($C_{15}H_{20}N_2OCl_2$)

|  | % C | % H | % N |
|---|---|---|---|
| Calcd. | 57.15 | 6.39 | 8.89 |
| Found | 56.82 | 7.04 | 8.63 | f) 2-(2,3-Dihydroxypropyl)amino-5-amino-1-phenylbenzene Dihydrochloride
Yield: 0.48 g (90% of the theoretical)
Colorless oil CHN analysis ($C_{15}H_{20}N_2O_2Cl_2 \times H_2O$)

|  | % C | % H | % N |
|---|---|---|---|
| Calcd. | 51.58 | 6.35 | 8.02 |
| Found | 52.18 | 6.8 | 7.87 |

Examples 5 to 8

Hair Colorants

Hair colorants solutions of the following composition were prepared:

| 0.00125 mole | of developer of formula (I) according to Table 1 |
| 0.00125 mole | of coupler according to Table 1 |
| 10.0 g | of potassium oleate (8% aqueous solution) |
| 10.0 g | of ammonia (22% aqueous solution) |
| 10.0 g | of isopropanol |
| 0.3 g | of ascorbic acid |
| to 100.0 g | water |

Immediately before use, 30 g of the foregoing colorant solution was mixed with 30 g of 6% hydrogen peroxide solution. The mixture was then applied to bleached hair. After an exposure time of 30 min at 40° C., the hair was rinsed with water, washed with a commercial shampoo and dried. The resulting color shades are shown in Table 1.

TABLE 1

| EXAMPLE | DEVELOPER OF FORMULA (I) | COUPLER | SHADE OBTAINED |
|---|---|---|---|
| 5 | 2,5-diamino-1-phenylbenzene.2 HCl | 2-amino-4-(2'-hydroxyethyl)amino-anisole sulfate | dark-blue |

TABLE 1-continued

| EXAMPLE | DEVELOPER OF FORMULA (I) | COUPLER | SHADE OBTAINED |
|---|---|---|---|
| 6 | 2,5-diamino-1-phenylbenzene.2 HCl | resorcinol | dark-blond |
| 7 | 2,5-diamino-4-methyl-1-phenyl-benzene | resorcinol | dark blond |
| 8 | 2-di(2-hydroxyethyl)amino-5-amino-1-phenyl-benzene.2HCl | 2-amino-4-(2-hydroxyethyl)aminoanisole sulfate | blue |

Examples 9 to 14

Hair Colorants

Hair colors solutions of the following composition were prepared:

| | |
|---|---|
| 0.00125 mole | of developer of formula (I) according to Table 2 |
| 0.00125 mole | of coupler according to Table 2 |
| 1.000 g | of potassium oleate (8% aqueous solution) |
| 1.000 g | of ammonia (22% aqueous solution) |
| 1.000 g | of ethanol |
| 0.300 g | of ascorbic acid |
| to 100 g | water |

Immediately before use, 10 g of the foregoing colorant solution was mixed with 10 g of 6% hydrogen peroxide solution. The mixture was then applied to bleached hair. After an exposure time of 30 min at 40° C., the hair was rinsed with water, washed with a commercial shampoo and dried. The resulting color shades are shown in Table 2.

TABLE 2

| EXAMPLE | DEVELOPER OF FORMULA (I) | COUPLER | SHADE OBTAINED |
|---|---|---|---|
| 9 | 2,5-diamino-1-(hydroxy)phenylbenzene.2HCl | 1,3-diamino-4-(2-hydroxyethoxy)benzene | dark-blue |
| 10 | 2,5-diamino-1-(4-aminophenyl)benzene | resorcinol | dark-blond |
| 11 | 2,5-diamino-1-(2-methyl-4-hydroxyphenyl)benzene.2 HCl | resorcinol | dark-blond |
| 12 | 2,5-diamino-1-(4-fluorophenyl)benzene.2 HCl | 1,3-diamino-4-(2-hydroxyethoxy)benzene | dark-blue |
| 13 | 2,5-diamino-1-(3-methylphenyl)benzene.2 HCl | resorcinol | dark-blond |
| 14 | 2,5-diamino-1-(3-fluoro-4-methoxyphenyl)benzene 2.HCl | 1,3-diamino-4-(2-hydroxyethoxy)benzene | dark-blue |

Example 15

Hair Colorant

A hair colorant solution of the following composition was prepared:

| | |
|---|---|
| 0.160 g | of 2,5-diamino-1-phenylbenzene.2 HCl |
| 0.160 g | of 1,4-diamino-2-(2-hydroxyethyl)benzene sulfate |
| 0.137 g | of 1,3-dihydroxybenzene |
| 0.100 g | of 1,3-dihydroxy-2-methylbenzene |
| 0.100 g | of 2-amino-5-methylphenol |
| 10.000 g | of potassium oleate (8% aqueous solution) |
| 10.000 g | of ammonia (22% aqueous solution) |
| 10.000 g | of isopropanol |
| 0.300 g | of ascorbic acid |
| to 100.000 g | water |

Immediately before use, 30 g of the foregoing colorant solution was mixed with 30 g of 6% hydrogen peroxide solution. The mixture was then applied to bleached hair. After an exposure time of 30 min at 40° C., the hair was rinsed with water, washed with a commercial shampoo and dried. The hair had a blond shade.

Example 16

Hair Colorant

A hair colorant solution of the following composition was prepared:

| | |
|---|---|
| 0.320 g | of 2,5-diamino-1-phenylbenzene.2 HCl |
| 0.300 g | of 5-amino-2-methylphenol |
| 0.600 g | of 4-amino-3-methylphenol |
| 0.600 g | of 4-aminophenol |
| 0.100 g | of α-naphthol |
| 0.200 g | of 2-chloro-6-(ethylamino)-4-nitrophenol |
| 10.000 g | of potassium oleate (8% aqueous solution) |
| 10.000 g | of ammonia (22% aqueous solution) |
| 10.000 g | of isopropanol |
| 0.300 g | of ascorbic acid |
| to 100.000 g | water |

Immediately before use, 30 g of the foregoing colorant solution was mixed with 30 g of 6% hydrogen peroxide solution. The mixture was then applied to bleached hair. After an exposure time of 30 min at 40° C., the hair was rinsed with water, washed with a commercial shampoo and dried. The hair had a red shade.

Example 17

Hair Colorant

A hair colorant solution of the following composition was prepared:

| | |
|---|---|
| 0.320 g | of 2,5-diamino-1-phenylbenzene.2 HCl |
| 0.040 g | of 5-amino-2-methylphenol |
| 0.090 g | of 2-amino-(2'-hydroxyethyl)aminoanisole sulfate |
| 0.030 g | of 3-aminophenol |
| 0.030 g | of 1,3-dihydroxybenzene |
| 0.040 g | of 1,3-dihydroxy-5-methylbenzene |
| 0.100 g | of 4-amino-5-methylphenol |
| 0.002 g | of 2-amino-3-methylphenol |
| 0.100 g | of 2-amino-6-methylphenol hydrochloride |
| 0.010 g | of 4-chloro-N-(2-hydroxyethyl)-2-nitroaniline |
| 0.020 g | of 2-amino-4,6-dinitrophenol |
| 0.100 g | of 2-chloro-6-(ethylamino)-4-nitrophenol |
| 10.000 g | of potassium oleate (8% aqueous solution) |
| 10.000 g | of ammonia (22% aqueous solution) |
| 10.000 g | of isopropanol |
| 0.300 g | of ascorbic acid |
| to 100.000 g | water |

Immediately before use, 30 g of the foregoing colorant solution was mixed with 30 g of 6% hydrogen peroxide solution. The mixture was then applied to bleached hair.

After an exposure time of 30 min at 40° C., the hair was rinsed with water, washed with a commercial shampoo and dried. The hair had a brown shade.

Example 18

Hair Colorant

A hair colorant solution of the following composition was prepared:

| | |
|---|---|
| 0.320 g | of 2,5-diamino-1-phenylbenzene.2 HCl |
| 0.040 g | of 5-amino-2-methylphenol |
| 0.050 g | of 1,3-diamino-4-(2-hydroxyethyl)benzene |
| 0.030 g | of 3-aminophenol |
| 0.030 | of 1,3-dihydroxybenzene |
| 0.040 g | of 1,3-dihydroxy-2-methylbenzene |
| 0.100 g | of 4-amino-5-methylphenol |
| 0.200 g | of 2-amino-3-methylphenol |
| 0.100 g | of 2-amino-6-methylphenol hydrochloride |
| 0.010 g | of 4-chloro-N-(2-hydroxyethyl)-2-nitroaniline |
| 0.020 g | 2-amino-4,6-dinitrophenol |
| 0.100 g | 2-chloro-6-(ethylamino)-4-nitrophenol |
| 10.000 g | of ammonia (22% aqueous solution) |
| 10.000 g | of isopropanol |
| 0.300 g | of ascorbic acid |
| to 100.000 g | water |

Immediately before use, 30 g of the foregoing colorant solution was mixed with 30 g of 6% hydrogen peroxide solution. The mixture was then applied to bleached hair. After an exposure time of 30 min at 40° C., the hair was rinsed with water, washed with a commercial shampoo and dried. The hair had a brown shade.

Example 19

Hair Colorant

A hair colorant solution of the following composition was prepared:

| | |
|---|---|
| 0.220 g | of 2,5-diamino-1-phenylbenzene.2 HCl |
| 0.100 g | of 1,4-diamino-2-(2-hydroxyethyl)benzene sulfate |
| 0.020 g | of 5-amino-2-methylphenol |
| 0.010 g | of 1,3-diamino-4-(2-hydroxyethoxy)benzene |
| 0.004 g | of 2-amino-4-(2'-hydroxyethyl)aminoanisole sulfate |
| 0.020 g | of 1,3-dihydroxybenzene |
| 0.040 g | of 1,3-dihydroxy-2-methylbenzene |
| 0.008 g | of 4-amino-3-methylphenol |
| 10.000 g | of potassium oleate (8%) aqueous solution) |
| 10.000 g | of ammonia (22% aqueous solution) |
| 10.000 g | of isopropanol |
| 0.300 g | of ascorbic acid |
| to 100.000 g | water |

Immediately before use, 30 g of the foregoing colorant solution was mixed with 30 g of 6% hydrogen peroxide solution. The mixture was then applied to bleached hair. After an exposure time of 30 min at 40° C., the hair was rinsed with water, washed with a commercial shampoo and dried. The hair had a brown shade.

Example 20

Hair Colorant

A hair colorant solution of the following composition was prepared:

| | |
|---|---|
| 0.220 g | of 2,5-diamino-1-phenylbenzene.2 HCl |
| 0.100 g | of 4-di-(2-hydroxyethyl)aminoaniline sulfate |

-continued

| | |
|---|---|
| 0.020 g | of 5-amino-2-methylphenol |
| 0.010 g | of 1,3-diamino-4-(2-hydroxyethyl)benzene |
| 0.015 g | 2-amino-4-(2'-hydroxyethyl)aminoanisole sulfate |
| 0.020 g | 1,3-dihydroxybenzene |
| 0.040 g | of 1,3-dihydroxy-2-methylbenzene |
| 0.008 g | of 4,5-diamino-1-(2-hydroxyethyl)-1H-pyrazole sulfate |
| 10.000 g | of potassium oleate (8%) aqueous solution) |
| 10.000 g | of ammonia (22% aqueous solution) |
| 10.000 g | of isopropanol |
| 0.300 g | of ascorbic acid |
| to 100.000 g | water |

Immediately before use, 30 g of the foregoing colorant solution was mixed with 30 g of 6% hydrogen peroxide solution. The mixture was then applied to bleached hair. After an exposure time of 30 min at 40° C., the hair was rinsed with water, washed with a commercial shampoo and dried. The hair had a brown shade.

Example 21

Hair Colorant

A hair colorant solution of the following composition was prepared:

| | |
|---|---|
| 0.320 g | of 2,5-diamino-1-phenylbenzene.2 HCl |
| 0.020 g | of 5-amino-2-methylphenol |
| 0.010 g | of 1,3-diamino-4-(2-hydroxyethoxy)benzene |
| 0.015 g | of 2-amino-4-(2'-hydroxyethyl)aminoanisole sulfate |
| 0.020 g | of 1,3-dihydroxybenzene |
| 0.040 g | of 1,3-dihydroxy-2-methylbenzene |
| 0.008 g | of 4-amino-2-(aminomethyl)phenol dihydrochloride |
| 10.000 g | of potassium oleate (8%) aqueous solution) |
| 10.000 g | of ammonia (22% aqueous solution) |
| 10.000 g | of isopropanol |
| 0.300 g | of ascorbic acid |
| to 100.000 g | water |

Immediately before use, 30 g of the foregoing colorant solution was mixed with 30 g of 6% hydrogen peroxide solution. The mixture was then applied to bleached hair. After an exposure time of 30 min at 40° C., the hair was rinsed with water, washed with a commercial shampoo and dried. The hair had a brown shade.

Unless otherwise indicated, all percentages are by weight.

What is claimed is:

1. Coloring agent for the oxidative coloring of keratinic fibers based on a developer/coupler comibination, characterized in that it contains as the developer a 2,5-diamino-1-phenylbenzene derivative of general formula (I)

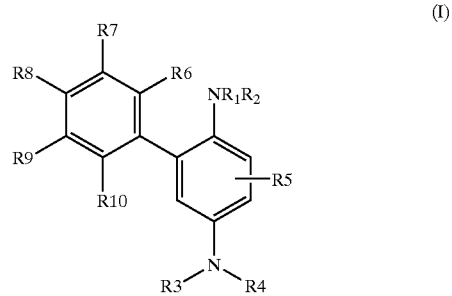

wherein

R1, R2, R3 and R4 independently of each other denote hydrogen, a C1–C6 alkyl, C1–C4 hyroxyalkyl, C2–C4 dihydroxyalkyl or C1–C4 alkoxy-(C1–C4) alkyl group, or R1 and R2 or R3 and R4 form a four-membered to eight-membered aliphatic ring, with at least two of the R1 to R4 groups denoting hydrogen;

R5 denotes hydrogen, a hydroxyl group, a halogen atom or a C1–C4 alkyl, C1–C4 hyroxyalkyl or C1–C4 alkoxy group;

R6, R7, R8, R9 and R10 independently of each other denote hydrogen, a halogen atom or a cyano, hydroxyl, C1–C4 alkoxy, C1–C6 alkyl, C1–C4 alkyl thioether, mercapto, nitro, amino, alkylamino, dialkylamino, trifluoromethane, —C(OH), —C(O)CH3, —C(O)CF3, —Si(CH)3, C1–C4 hydroxyalkyl, C3–C4 dihydroxyalkyl, —CH═CHR11 or —(CH2)p-CO2R12 group or a —(CH2)p—R13 group, where p=1, 2, 3 or 4, or a —C(R14)═NR15 group or a C(R17)H—NR18R19 group, or two adjacent R6 to R10 groups form a —O—CH2—O bridge; with the proviso that at least one of R6 and R9 is not an amino group if R1, R2, R3 and R4 are hydrogen;

R11 denotes hydrogen, a hydroxyl, nitro, amino, CO2R12 or —C(O)CH3 group;

R12, R14 and R17 independently of each other denote hydrogen or a C1–C4 alky group;

R13 denotes an amino or nitrile group;

R15, R18 and R19 independently of each other denote hydrogen, a hydroxyl, C1–C4 alkyl, C1–C6 hydroxyalkyl or C3–C4 dihydroxyalkyl group or a radical of formula

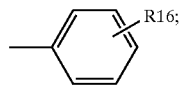

and

R16 denotes hydrogen, an amino group or a hydroxyl group or a physiologically acceptable, water-soluble salt thereof.

2. Coloring agent according to claim 1, characterized in that R5 denotes hydrogen.

3. Coloring agent according to claim 1, characterized in that either both radicals R1 and R2 or both radicals R3 and R4 denote hydrogen.

4. Coloring agent according to claim 1, characterized in that radicals R1 to R4 all denote hydrogen.

5. Coloring agent according to claim 1, characterized in that four of the radicals R6 to R10 denote hydrogen and that the fifth of said radicals R6 to R10 denotes hydrogen, a —C(O)H group, a —C(O)CH3 group, a C1–C4 alkyl group or a C1–C4 hydroxyalkyl group.

6. Coloring agent according to claim 1, characterized in that the 2,5-diamino-1-phenylbenzene derivative of formula (I) is selected from among 2,5-diamino-1-phenylbenzene; 2,5-diamino-1-(3-nitrophenyl)bezene, 2,5-diamino-1-(4-methoxy-phenyl)benzene; 2,5-diamino-1-(3-methoxyphenyl)benzene; 2,5-diamino-1-(3-amino-phenyl)benzene; 2,5-diamino-1-(2-methylphenyl)benzene; 2,5-diamino-1-(3-methylphenyl)benzene; 2,5-diamino-1-(4-methylpheyl)benzene; 2,5-diamino-1-(3-chlorophenyl)benzene and 2,5-amino-1-(4-chlorophenyl)benzene, and physiologically acceptable salts thereof.

7. Coloring agent according to claim 1, characterized in that it contains the diaminobenzene derivative of formula (I) in an amount from 0.005 to 20.0 wt %.

8. Coloring agent according to claim 1, characterized in that it contains besides the 1,4-diaminobenzene derivative of formula (I) also at least one additional developer selected from among 1,4-diaminobenzene, 2,5-diaminotoluene, 2,5-diaminophenylethyl alcohol, 4-aminophenol and derivatives thereof, 4,5-diaminopyrazol derivatives and tetraaminopyrimidines.

9. Coloring agent according to claim 1, characterized in that it contains the developers and couplers in a total amount from 0.005 to 20.0 wt %, based on the total amount of oxidative coloring agent.

10. Coloring agent according to claim 1, characterized in that it contains additionally at least one direct dye.

11. Coloring agent according to claim 1, characterized in that it has a pH from 6.8 to 11.5.

12. Coloring agent according to claim 1, characterized in that it is in the form of an aqueous or aqueous-alcoholic solution, a cream, a gel or an emulsion.

13. Coloring agent according to claim 1, characterized in that it is a hair colorant.

14. 2,5-Diamino-1-phenylbenzene derivatives of formula (I) according to claim 1 wherein at least one of radicals R1 to R10 is different from hydrogen, or physiologically tolerated water-soluble salts thereof.

* * * * *